United States Patent
Pasternak et al.

(10) Patent No.: US 6,627,734 B1
(45) Date of Patent: Sep. 30, 2003

(54) IDENTIFICATION AND CHARACTERIZATION OF MULTIPLE SPLICE VARIANTS OF THE KAPPA$_3$-RELATED OPIOID RECEPTOR (KOR-3) GENE

(75) Inventors: Gavril Pasternak, New York, NY (US); Ying-Xian Pan, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 09/743,871

(22) PCT Filed: Jul. 15, 1999

(86) PCT No.: PCT/US99/15977

§ 371 (c)(1),
(2), (4) Date: Mar. 13, 2001

(87) PCT Pub. No.: WO00/04151

PCT Pub. Date: Jan. 27, 2000

Related U.S. Application Data

(60) Provisional application No. 60/093,002, filed on Jul. 16, 1998.

(51) Int. Cl.$^7$ .................................. C07K 1/00
(52) U.S. Cl. ........................ 530/350; 435/6; 435/7.1; 435/7.21; 435/69.5; 435/252.3; 435/320.1; 436/501; 514/2; 514/44; 530/23.5
(58) Field of Search ................ 536/23.5; 530/350; 435/6, 7.1, 7.21, 69.5, 252.3, 320.1; 436/501; 514/2, 44

(56) References Cited

U.S. PATENT DOCUMENTS

| | | |
|---|---|---|
| 4,946,778 A | 8/1990 | Ladner et al. |
| 5,747,279 A | 5/1998 | Pasternak et al. |

FOREIGN PATENT DOCUMENTS

| | | |
|---|---|---|
| WO | WO 94/28132 | 12/1994 |
| WO | WO 95/12616 | 5/1995 |

OTHER PUBLICATIONS

Bowie et al., 1990, Science 247:1306–1310, especially p. 1306.*
Alexander et al., Proc. Natl. Acad. Sci. 89(3352–3356)1992.*
Mollereau et al., FEBS Letters 341(33–38)1994.*
Pan et al., Molecular Pharmacology, 1180–1188, 1995.*
Bare et al. (1994) "Expression of two variants of the human $\mu$ opioid receptor mRNA in SK–N–SH cells and human brain" FEBS Lett. 354:213–6.
Bunzow et al. (1994) "Molecular cloning and tissue distribution of a putative member of the rat opioid receptor gene family that is not a $\mu$, $\delta$ or $\kappa$ or an opioid receptor type" FEBS Lett. 347:284–288.
Capecchi (1989) "Altering the genome by homologous recombination" Science 244:1288.
Chen et al. (1993) "Molecular cloning and functional expression of a $\mu$–opioid receptor from rat brain" Mol. Pharmacol. 44:8–12.
Chomczynski et al. (1987) "Single–step method of RNA isolation by acid guanidinium thiocyanate–phenol–chloroform extraction" Anal. Biochem. 162:156–9.
Cole et al. (1985) "The EBV–hybridoma technique and its application to human lung cancer" in "Monoclonal Antibodies and Cancer Therapy" Alan R. Liss, Inc., pp. 77–96).
Cote et al. (1983) "Generation of human monoclonal antibodies reactive with cellular antigens" Proc. Natl. Acad. Sci. U.S.A. 80:2026–2030.
Delfs et al. (1994) "Expression of $\mu$ opioid receptor mRNA in rat brain: an in situ hybridization study at the single cell level" J. Comp. Neurol. 345:46–68.
Elliott et al. (1994) "The NMDA receptor antagonists, LY274614 and MK–801, and the nitric oxide synthase inhibitor, NG–nitro–L–arginine, attenuate analgesic tolerance to the mu–opioid morphine but not to kappa opioids" Pain 56:69–75.
Evans et al. (1981) "Establishment in culture of pluripotential cells from mouse embryos" Nature 292:154–6.
Fukuda et al. (1994) "cDNA cloning and regional distribution of a novel member of the opioid receptor family" FEBS Lett. 343:42–46.
Gaveriaux–Ruff et al. (1997) "Detection of opioid receptor mRNA by RT–PCR reveals alternative splicing for the $\delta$ and $\kappa$ –opioid receptors" Molec. Brain Res. 48:298–304.
Grisel et al. (1996) "Orphanin FQ acts as a supraspinal, but not a spinal, anti–opioid peptide" NeuroReport 7:2125–2129.
Guiramand et al. (1995) "Alternative splicing of the dopamine D2 receptor directs specificity of coupling to G–proteins" J. Biol. Chem. 270:7354–58.
Halford et al. (1995) "Functional role and sequence analysis of a lymphocyte orphan opioid receptor" J. Neuroimmunol. 59:91–101.
Huse et al. (1989) "Generation of a large combinatorial library of the immunoglobulin repertoire in phage lambda" Science 246:1275–81.
Jaenisch (1988) "Transgenic animals" Science 240:1468–74.

(List continued on next page.)

Primary Examiner—Yvonne Eyler
Assistant Examiner—Michael Brannock
(74) Attorney, Agent, or Firm—Frommer Lawrence & Haug LLP

(57) ABSTRACT

The present invention encompasses novel splice variant forms of the muopioid receptor-1 (KOR-3) and the polynucleotide sequences encoding the KOR-3 splice variants. The invention further encompasses methods of screening for compositions regulating the KOR-3 splice variant activities and the development of therapeutic modalities directed to regulating activity. Regulation of the KOR-3 splice variant activities may impact the physiologic processes of analgesia and weight management.

17 Claims, 15 Drawing Sheets

OTHER PUBLICATIONS

King et al. (1998) "Functional blockade of opioid analgesia by orphanin FQ/nociceptin" Biochem. Pharmacol. 55:1537–40.

King et al. (1997) "Spinal analgesic activity of orphanin FQ/nociceptin and its fragments" Neurosci. Lett. 223:113–116.

Kohler et al. (1975) "Continuous cultures of fused cells secreting antibody of predefined specificity" Nature 256–495.

Kolesnikov et al. (1994) "1–Aminocyclopropane carboxylic acid (ACPC) prevents $\mu$ and $\delta$ opioid tolerance" Life Sci. 55:1393–98.

Kolesnikov et al. (1993) "Blockade of tolerance to morphine but not to kappa opioids by a nitric oxide synthase inhibitor" Proc. Natl. Acad. Sci. U.S.A. 90:5162–5166.

Kozbor et al. (1983) "The production of monoclonal antibodies from human lymphocytes" Immunol. Today 4:72.

Lucas et al. (1995) "New players in the 5–HT receptor field: genes and knockouts" TiPS 16:246–252.

Lutz et al. (1992) "Opioid receptors and their pharmacological profiles" J. Receptor Res. 12:267–286.

Mathis et al. (1997) "Biochemical evidence for orphanin FQ/nociceptin receptor heterogeneity in mouse brain" Biochem. Biophys. Res. Commun. 230:462–5.

McCullough et al. (1997) "G triplets located throughout a class of small vertebrate introns enforce intron borders and regulate splice site selection" Molec. Cell. Biol. 17:4562–4571.

Meunier et al. (1995) "Isolation and structure of the endogenous agonist of opioid receptor–like $ORL_1$ receptor" Nature 377:532–535.

Mogil et al. (1996) "Functional antagonism of $\mu$, $\delta$–or $\kappa$–opioid antinociception by orphanin FQ" Neurosci. Lett. 214:1–4.

Mogil et al. (1996) "Orphanin FQ is a Functional Anti–Opioid Peptide" Neurosci. 75:333–337.

Mollereau et al. (1994) "ORL1, a novel member of the opioid receptor family" FEBS Lett. 341:33–38.

Morrison et al. (1984) "Chimeric human antibody molecules: mouse antigen–binding domains with human constant region domains" Proc. Natl. Acad. Sci. U.S.A. 81:6851–55.

Neuberger et al. (1984) "Recombinant antibodies possessing novel effector functions" Nature 312:604–8.

Olson et al. (1989) "Endogenous opiates: 1988" Peptides 10:1253–1280.

Pan et al. (1996) "Structure and characterization of gene encoding a mouse $kappa_3$–related opioid receptor" Gene 171:255–260.

Pan et al. (1996) "Dissociation of affinity and efficacy in KOR–3 chimeras" FEBS Lett. 395:207–10.

Pan et al. (1995) "Cloning and Functional Characterization Through Antisense Mapping of a $\kappa_3$–Related Opioid Receptor" Mol. Pharmacol. 47:1180–1188.

Pan et al. (1994) "Cloning, expression and classification of a Kappa3–related opioid receptor using antisense oligodeoxynucleotides" Regul. Pept. 54:217–218.

Pasternak et al. (1995) "Mapping of opioid receptors using antisense oligodeoxynucleotides: correlating their molecular biology and pharmacology" TiPS 16:344–50.

Pasternak (1993) "Pharmacological mechanisms of opioid analgesics" Clin. Neuropharmacol. 16:1–18.

Reinscheid et al. "Orphanin FQ: A neuropeptide that activates an opioidlike G protein–coupled receptor" (1995) Science 270:792–794.

Reisine et al. (1996) "Opioid analgesics and antagonists" in Goodman & Gilman's "The pharmacological basis of therapeutics" Ninth Edition (Hardman et al. eds.) McGraw–Hill pp. 521–555.

Reisine et al. (1993) "Molecular Biology of opioid receptors" Trends Neurosci. 16:506–510.

Robertson (1991) "Using embryonic stem cells to introduce mutations into the mouse germ line" Biol. Reprod. 44:238–245.

Rossi et al. (1997) "Antisense mapping of MOR–1 in rats: distinguishing between morphine and morphine–6$\beta$–glucuronide antinociception" J. Pharmacol. Exp. Ther. 281:109–114.

Rossi et al. (1994) "Blockade of Morphine Analgesia by an Antisense Oligodeoxynucleotide Against the Mu Receptor" Life Sci. 54:375–379.

Rossi et al. (1996) "Novel receptor mechanisms for heroin and morphine–6$\beta$–glucuronide analgesia" Neurosci. Lett. 216:1–4.

Rossi et al. (1996) "Naloxone sensitive orphanin FQ–induced analgesia in mice" Eur. J. Pharmacol. 311:R7–8.

Sibinga et al. (1988) "Opioid peptides and opioid receptors in cells of the immune system" Annu. Rev. Immunol. 6:219–49.

Simon (1991) "Opioid receptors and endogenous opioid peptides" Med. Res. Rev. 11:357–374.

Standifer et al. (1997) "G proteins and opioid receptor–mediated signaling" Cell. Signal. 9:237–248.

Standifer et al. (1996) "Differential blockade of opioid analgesia by antisense oligodeoxy–nucleotides directed against various G protein $\alpha$ subunits" Mol. Pharmacol. 50:293–298.

Takeda et al. (1985) "Construction of chimaeric processed immunoglobulin genes containing mouse variable and human constant region sequences" Nature 314:452–4.

Tian et al. (1997) "Bidirectional modulatory effect of orphanin FQ on morphine–induced analgesia: antagonism in brain and potentiation in spinal cord of the rat" Br. J. Pharmacol. 120:676–80.

Trujillo et al. (1991) "Inhibition of morphine tolerance and dependence by the NMDA receptor antagonist MK–801" Science 251:85–87.

van den Engh et al. (1992) "Estimating genomic distance from DNA sequence location in cell nuclei by a random walk model" Science 257:1410–1412.

Vanetti et al. (1992) "Cloning and expression of a novel mouse somatostatin receptor (SSTR2B)" FEBS Lett. 311:290–294.

Wang, et al. (1994) "cDNA cloning of an orphan opiate receptor gene family member and its splice variant" FEBS Lett. 348:75–9.

Wick et al. (1994) "Isolation of novel cDNA encoding a putative membrane receptor with high homology to the cloned $\mu$, $\delta$ and $\kappa$ opioid receptors" Molec. Brain Res. 27:37–44.

Yamamoto et al. (1997) "Analgesic Effect of Intrathecally Administered Nociceptin, an Opioid Receptor–Like$_1$ Receptor Agonist, in the Rat Formalin Test" Neurosci. 81:249–254.

Yasuda et al. (1993) "Cloning and functional comparison of κ and δ opioid receptors from mouse brain" Proc. Natl. Acad. Sci. U.S.A. 90:6736–6740.

Zhu et al. (1997) "Orphanin FQ potentiates formalin–induced pain behavior and antagonizes morphine analgesia in rats" Neurosci. Lett. 235:37–40.

Zimprich et al. (1995) "Cloning and expression of an isoform of the rat μ opioid receptor (rMOR1B) which differs in agonist induced desensitization from RmOR1" FEBS Lett. 359:142–146.

Nishi et al. (1994) "Structure and chromosomal mapping of genes for the mouse kappa–opioid receptor and an opioid receptor homologue (MOR–C)" Biochem. Biophys. Res. Commun. 205:1353–1357.

Pan et al. (1996) "Mus musculus opioid receptor (KOR–3) gene, exon 1" Database EMBL–EMROD (Online) Entry MMUOR3SO2, Acc. No. U32926.

Pan et al. (1996) "Mus musculus opioid receptor (KOR–3) gene, exon 2" Database EMBL–EMROD (Online) Entry MMURO3SO4, Acc. No. U 32928.

Pan et al. (1996) "Mus musculus opioid receptor (KOR–3) gene, exon 3" Database EMBL–EMROD (Online) Entry MMUOR3SO6, Acc. No. U 32930.

Pan et al. (1998) "Identification and differential regional expression of KOR–3/ORL–1 gene splice variants in mouse brain" FEBS Lett. 435:65–68.

Pasternak et al. (1996) "the KOR–3 receptor and the kappa3–opioid receptor may be splice variants of the same gene" Trends Pharm. Sci. 17:217–218.

Peluso et al. (1997) "Distribution of nociceptin/orphanin FQ receptor transcript in human central nervous system and immune cells" J. Neuroimmunol. 81:184–192.

European Search Report Sep. 17, 2001, EP 99934046.

Pan et al. Genbank Accession U32928, Jul. 28, 1996.

Pan et al. Genbank Accession U32930, Jul. 28, 1996.

Ying–Xian et al. "Identification and differential regional expression of KOR–3/ORL–1 gene splice variants in mouse brain" FEBS Letters 435 (1998) 65–68.

Peluso et al. "Distribution of nociceptin/orphanin FQ receptor transcript in human central nervous system and immune cells" Journal of Neuroimmunology 81 (1998) 184–192.

Pan et al., Genbank Accession U32926. Aug. 1995.

Pan, Y–X, et al. FEBS Letters, 395, 207–210, 1996.

* cited by examiner

MLATVPSCPLDSRSPSWGSTWLCASGGSWGTASSCMSSSAGRALRGTGDSRHTKMKTATN
IYIFNLALADTLVLLTLPFQGTDILLGFWPFGNALCKTVIAIDYYNMFTSTFTLTAMSVD
RYVAICHPIRALDVRTSSKAQAVNVAIWALASVVGVPVAIMGSAQVEDEEIECLVEIPAP
QDYWGPVFAICIFLFSFIIPVLIISVCYSLMIRRLRGVRLLSGSREKDRNLRRITRLVLV
VVAVFVGCWTPVQVFVLVQGLGVQPGSETAVAILRFCTALGYVNSCLNPILYAFLDENFK
ACFRKFCCASALHREMQVSDRVRSIAKDVGLGCKTSETVPRPA

FIG. 2

MESLFPAPFWEVLYGSHFQGNLSLLNETVPHHLLLNASHSAFLPLGLKVTIVGLYLAVCI
GGLLGNCLVMYVILRQCPENPLRGVLRETEERRQHLSLLIPSTNSHSGTPR

FIG. 3

MESLFPAPFWEVLYGSHFQGNLSLLNETVPHHLLLNASHSAFLPLGLKVTIVGLYLAVCI
GGLLGNCLVMYVILRQHCALGRSLMNFTGSALKTL

FIG. 4

MESLFPAPFWEVLYGSHFQGNLSLLNETVPHHLLLNASHSAFLPLGLKVTIVGL
YLAVCIGGLLGNCLVMYVILRHTKMKTATNIYIFNLALADTLVLLTLPFQGTDI
LLGFWPFGNALCKTVIAIDYYNMFTSTFTLTAMSVDRYVAICHPIRALDVRTSS
KAQAVNVAIWALASVVGVPVAIMGSAQVEDEGQWAVLLPDQSVPHGSCRPL

FIG. 5

MLVTAPSCPLDSRSPSWGSTWLCASGGSWGTASSCMSSSAGRALRGTGDSRHTKMKTATN
IYIFNLALADTLVLLTLPFQGTDILLGFWPFGNALCKTVIAIDYYNMFTSTFTLTAMSVD
RYVAICHPIRALDVRTSSKAQAVNVAIWALASVVGVPVAIMGSAQVEDEEIECLVEIPAP
QDYWGPVFAICIFLFSFIIPVLIISVCYSLMIRRLRGVRLLSGSREKDRNLRRITRLVLV
VVAVFVGCWTPVQVFVLVQGLGVQPGSETAVAILRFCTALGYVNSCLNPILYAFLDENFK
ACFRKFCCASSLHREMQVSDRVRSIAKDVGLGCKTSETVPRPA

FIG. 6

MPATAPSCPSGSRSPSWGSTWPCVSEGSWGTALSCTSSSGRLGPKVPVWHTKMKTATNIY
IFNLALADTLVLLTLPFQGTDILLGFWPFGNALCKTVIAIDYYNMFTSTFTLTAMSVDRY
VAICHPIRALDVRTSSKAQAVNVAIWALASVVGVPVAIMGSAQVEDEEIECLVEIPTPQD
YWGPVFAICIFLFSFIVPVLVISVCYSLMIRRLRGVRLLSGSREKDRNLRRITRLVLVVV
AVFVGCWTPVQVFVLAQGLGVQPSSETAVAILRFCTALGYVNSCLNPILYAFLDENFKAC
FRKFCCASALRRDVQVSDRVRSIAKDVALACKTSETVPRPA

FIG. 7

MEPLFPAPFWEVIYGSHLQGNLSLLSPNHSLLPPHLLLNASHGAFLPLGLKVTIVGLYL
AVCVGGLLGNCLVMHTKMKTATNIYIFNLALADTLVLLTLPFQGTDILLGFWPFGNALC
KTVIAIDYYNMFTSTFTLTAMSVDRYVAICHPIRALDVRTSSKAQAVNVAIWALASVVG
VPVAIMGSAQVEDEEIECLVEIPTPQDYWGPVFAICIFLFSFIVPVLVISVCYSLMIRR
LRGVRLLSGSREKDRNLRRITRLVLVVVAVFVGCWTPVQVFVLAQGLGVQPSSETAVAI
LRFCTALGYVNSCLNPILYAFLDENFKACFRKFCCASALRRDVQVSDRVRSIAKDVALA
CKTSETVPRPA

```
   1  tttgcttcct tctccaacct gcgcagcccc tccttctctc agccgcagcc ttctgccc
  61  tccccttctt ggctgccgca ctggctgctg cgtctagtca atatcttatc ttcgagcag
 121  gagctaggag ccattcccag ccggagcaga ccccaagcta gagtgagaag cattactcag
 181  ttcattgtgc tcctgcctgt cttctgcta agcattaggg tctgttttgg cccagcttct
 241  gaagaggttg tgtgtgctgt tggaggaact gtactgagtg gctttgcagg gtgacagcat
 301  ggagtccctc ttcctctctc ctaaatgaga cattctggga ggtcttgtat ttcaaggaa
 361  cctgtctgcc cttcctcctg gggactcca ccgtaccca tcaccctgct tgccacagtg
 421  cttccagctt ggacactggc gggaactgac aggtcaccat agctgggagg ggccatcgg
 481  ggcattggag gaactgaga tgataccgc ctcgtcatga agctggctg tgtcatccc
 541  gaactggct tggcacttctg gccattggg accaagatga cactgactga agctgctac
 601  tgggctgcc cagcactgg gccacttcctt actttgactg ccatggtgt ccatggtact
 661  tgggctctg ccgcacctcg gatgttcgga catgcaggg agaccggt catccagcc
 721  acatgttac acattatat ccgttccctg gtgtttgtgg caagaggct catcatggc
 781  gccaccttg cagtctgcct gataccgc caccttctct cctcatcat agccaggac
 841  ccatatggc aggatacctt aggacttc cgcttttcca gatccccgc ttcctgttc
 901  tggagtgga agagatcgag gcgtctgcag gcactctgcc cttcctgttgg cccgctcc
 961  ctgtatttcc catctgcatc cctcatgatt gactacttcg ctgcttcca ggctgcttcag
1021  tctgctacag gaacctgcga gaacctgccg cgcatcacac cttggctgcc ggcctgaac
1081  agaaggaccg gacacctgtg cagctcgttg caggtcttttg ggctagttgt gctgtgtttg
1141  tgggctgctg gcactgagc attctgcgct caggttcctg aggactggat gttcagccag
1201  gtagtgagac tgcagtagcc tgcagtagcc gcttctctat caagggacct cgaagcattg
1261  gtctcaatcc cattttctat caggttctgg ctgacccctg tgacccctg cgcagcattg
1321  tctgctgtgt aggccttggt agctctcctg tgcaggtggt tgaagaacagt gcatgactag
1381  ccaaggatgt aggccttggt aggccttggt gcaaggcttgg caggtctgg accacgccg acctttagc
1441  gcgtggacct gccatggtg accatggac aagtctcagtc ctaaggaag accatgggac
```

```
1501 aggtcaaagc atcaaggtgg cctccatggc tctgtcagat taagtttcct ccctggtata
1561 ggaccagaga gaaccaaagg aactgcatgg aaacatccac aactcagtgg acatgcctgg
1621 tgaaccatg taggtattca tggttcactt gactcttctc tggtttctcc ctgctgccct
1681 ggttctaggt gggctcagct gaggtattgt agttgtcatg tagtcactat tgtgactacc
1741 tgtttctaggt ggcctccctc agccttcagt gtttgcacac aactggtgat catacccagt
1801 gttgcctggc cctaagctt ggagttgcct ggagcatct agttctgact ccactgatgc
1861 attcagatta cctgagtgg gtgagcatca gtgggttctt ggatgactgt ttcctgacga
1921 ttcttttcat gctgtactat ggtgtatatg aagggactt cacacttcat ctggtactgc
1981 cactgcctgc tctaccaacc ggtaccaccg tggaccacct tctcagcaag aggctagcag gggacaaga
2041 cacaaagct cctaaggct cttttcccctcc taactcttta aggagaaaat tctgtgcct
2101 tgtttggcaa gccctgcttc aactgtgtg aggagtaatc ttgggtatgt gtcttgcttg
2161 ctgtaggctg ctcacagcat ggaggcacca catgctggtc ttattctcca cagcctccct
2221 ctcagtatgg gcagggcagg gcacgagact atctctctcc cagtagaggt tgtactcgta
2281 cagctctcca gcagtcgctc gtttactga cagtagatgt gttctattct ataccacag
2341 gaaacacact tgtagcccgg gaagactgga gtcaggatgg caaggcctgg gcttgcaagg
2401 tgaccacctg cttcatttat agggttagga catatccaag catttgagca atctgcaagg
2461 aaatgaagag ctgtatgag agctgaagcc taaaatggct gagtcgatac cttggagata tatgttggt
2521 actattacgg tttggggac attggaagaa gagtcgatac ttctatgggt cagataaaa aaaa
2581 tcacagaaga agaggcttg taaatgccct
```

FIG. 9B

```
   1  tggctttgca gggtgacagc atggagtccc tctttcctgc cccattctgg gaggtcttgt
  61  atggcagcca ctttcaaggg aacctgtctc tcctaaatga gaccgtaccc catcacctgc
 121  tcctcaatgc tagccacagt gccttcctgc cccttgact caaggtcacc atcgtggggc
 181  tctacttggc tgtgtgcatc gggggctcc tggggaactg cctcgtcatg tatgtcatcc
 241  tcaggcagtg ccctgaaaac cctctgagag gagtcttaag agagactgag gagagaagac
 301  gcatctctc tctcttgatt cttccacaa attcacattc aggcacacca agatgaagac
 361  tgctaccaac atttacatat ttaatctggc actggctgat accctgtctt tgctgacact
 421  gcccttccag ggcacagaca tccttctggg cttctggcca tttgggaatg cactgtgcaa
 481  gacggtcatt gctatcgact actacaacat gttttaccagc actttcactt tgactgccat
 541  gagtgtagac cgttatgtag ctatctgcca cccctatccgt gcccttgatg ttcggacatc
 601  cagtaaaagcc caggccgtta atgtggccat atgggccctg gcttcggtgg ttggtgttcc
 661  tgttgccatc atgggctcag cacaagtgga ggatgaagag atcgagtgcc tggtggagat
 721  ccccgccccct caggactatt gggcccctgt atttgccatc tgcatcttcc ttttttcctt
 781  catcatcccg gttctgatca ctatctgcca cccgagagaa ggaccggaac atgattcgac gacttcgtgg
 841  tgtccggctg ctttcaggct cccgagagaa ggaccggaac ctgcgacgca tctttgtcct
 901  ggtactggta gttgtggctg tgttttgtgg ctgctggaca cctgtggagg tagccattc tgcgcttctg
 961  ggttcaagga ctgggtgttc agccagttg tgagactgca gtagactgca caatccatt tcttgatga
1021  cacagcccctg ggctatgtca acagttgtct caatcgtct ctctatgctt gccctgcacc gggagatgca
1081  gaacttcaag gcctgcttta gaaagttctg ctgtgctttct gccctgcacc cttggttgca agacctctga
1141  ggtttctgat cgtgtgcgca gcattgccaa ggatgtaggc cttggttgca atggtgcctg tcagtcc
1201  gacagtacca cggccggcat gactaggcgt gaccctgccc atggtgcctg tcagtcc
```

FIG. 10

```
   1 tggctttgca gggtgacagc atggagtccc tctttcctgc cccattctgg gaggtcttgt
  61 atggcagcca ctttcaaggg aacctgtctc tcctaaatga gaccgtaccc catcacctgc
 121 tcctcaatgc tagccacagt gccttcctgc cccttggact caaggtcacc atcgtgggc
 181 tctacttggc tgtgtgcatc ggggctctc tgggaactg cctcgtcatg tatgtcatcc
 241 tcagacaaca ttgtgcactt ggaagatctt tgatgaactt tacaggcagt gccctgaaaa
 301 ccctctgaga ggagtcttaa gagagactga ggagagaaga cagcatctct ctctcttgat
 361 tccttccaca aattcacatt caggcacacc aagatgaaga ctgctaccaa catttacata
 421 tttaatctgg cactggctga taccctggtc ttgctgacac tgcccttcca gggcacagac
 481 atccttctgg gcttctggcc atttgggaat gcactgtgca agacggtcat tgctatcgac
 541 gctatctgcc accctatccg tgcccttgat gttcggacat ccagtaaagc ccaggccgtt
 601 aatgtggcca tatgggccct ggcttcgtg gttggtgttc ctgttgccat catgggctca
 661 gcacaagtgg aggatgaaga gatcgagtgc ctggtggaga tccccgcccc tcaggactat
 721 tggggccctg tatttgccat ctgcatcttc cttttttcct tcatcatccc ggttctgatc
 781 atctctgtct gctacagcct catgattcga cgacttcgtg cgtccggct gctttcaggc
 841 tcccgagaga aggaccggaa cctgcgacgc atcacacggc gtgtactggt agttgtggct
 901 gtgtttgtgg gctgctggac acctgtgtcc acctttgtcc tggttcaagg actgggtgtt
 961 cagccaggta gtgagactgc agtagccatt tctctatgct ctgcgcttct gcacagccct
1021 aacagtttgt tcaatcccat tctgtgcttc ctcttgatg agaacttcaa ggcctgcttt
1081 agaaagttct gctgtgcttc tgccctgcac cgggagatgc aggtttctga tcgtgtgcgc
1141 agcattgcca aggatgtagg ccttggttgc aagacctctg gtcagtacc acggccggca
1201 tgactaggcg tggacctgcc catggtgcct gtctctctag gttgaccctg gtcagtccac
1261 acggagctca cacaggtcac tgctctctac caggatgctc agtcctagag aactgagcgt
1321 gaatggcttt tcttttggtt caggatgtc agtcctagag aagaccttt tagcaccatg
1381 ggacaggtca aagcatcaag gtggcctcca gtggcctgtc agattaagtt tcctccctgg
1441 tataggacca gagagaacca aggaactgc atggaaacat ccacaactca gtggacatgc
```

FIG. 11A

```
1501 ctggtgaacc catgtaggta ttcatggttc acttgactct tctctgtttt ctccctgctg
1561 ccctggttct agtgggctc agctgaggta ttgtagttgt catgtagtca ctattgtgac
1621 tacctgttgt gtgctattgc cctcagcctt cagtgtttgc acagaactgg tgatcatacc
1681 cagtgttgcc tggcccttaa gcttggagtt gccttggagc atctagttct gactccactg
1741 atgcattcag attacctgag gtgggtgagc atcagtgggt tctttggatga ctgttttcctg
1801 acgattcttt tcatgctgta ctatgtgta tatgaagggg acttcacact tcatctggta
1861 ctgccactgc ctgctctacc aacctggacc acctctcag caagaggcta gcaggggac
1921 aagacacaaa gcttccctaa ggctcttcc ctccaaaacc actgtgaact cttattctac
1981 agactgtttg gcaagccctg cttctaactg tgtgggaagt aatcaggaga aaattctgtg
2041 gcctctgtag gctgctcaca gcatggaggc accacatgct ggtcttgggt atgtgtcttg
2101 gctgctcagt atgggcaggg cagggcacga gactatctct ctccttattc tccacagcct
2161 ccctcagctc tccagcagtc gctcttttac ttgacagtag aggttagcag cagttgtact
2221 cgtagaaaca cacttgtagc ccgggaagac tggagtcagg atgtgttcta ttctatacccc
2281 acagtgacca cctgcttcat ttatagggtt aggacatatc caagcaaggc ctgggcttgg
2341 catcaaatga agagctggta tgagagctga agcctaaaat ggctcatttg agcaatctgc
2401 aaggactatt acggtttttgg ggacattgga agaagagtcg atacccttgga gatatattgt
2461 tggttcacag aagaagaggc tttgtaaatg cccttctctat gggtcagata aaaaaaaa
```

FIG. 11B

```
GTACTGAGTGGCTTTGCAGGGTGACAGCATGGAGTCCCTCTTTCCTGCTCCATACTGGGA
GGTCTTGTATGGCAGCCACTTTCAAGGGAACCTGTCCCTCCTAAATGAGACCGTACCCCA
CCACCTGCTCCTCAATGCTAGTCACAGCGCCTTCCTGCCCCTTGGACTCAAGGTCACCAT
CGTGGGGCTCTACTTGGCTGTGTGCATCGGGGGGCTCCTGGGGAACTGCCTCGTCATGTA
TGTCATCCTCAGCTGGGAGGGCATTGAGGGGGACTGGAGACAGCAGGCACACCAAGATGA
AGACAGCTACCAACATTTACATATTTAATCTGGCACTGGCTGATACCCTGGTCTTGCTAA
CACTGCCCTTCCAGGGCACAGACATCCTACTGGGCTTCTGGCCATTTGGGAATGCACTCT
GCAAGACTGTCATTGCTATCGACTACTACAACATGTTTACCAGCACTTTTACTCTGACCG
CCATGAGCGTAGACCGCTATGTGGCTATCTGCCACCCTATCCGTGCCCTTGATGTTCGGA
CATCCAGCAAAGCCCAGGCTGTTAATGTGGCCATATGGGCCCTGGCTTCAGTGGTTGGTG
TTCCTGTTGCCATCATGGGTTCAGCACAAGTGGAAGATGAAGAGATCGAGTGCCTGGTGG
AGATCCCTGCCCCTCAGGACTATTGGGGCCCTGTATTCGCCATCTGCATCTTCCTTTTTT
CCTTCATCATCCCTGTGCTGATCATCTCTGTCTGCTACAGCCTCATGATTCGACGACTTC
GTGGTGTCCGTCTGCTTTCAGGCTCCCGGGAGAAGGACCGAAACCTGCGGCGTATCACTC
GACTGGTGCTGGTAGTGGTGGCTGTGTTTGTGGGCTGCTGGACGCCTGTGCAGGTGTTTG
TCCTGGTTCAAGGACTGGGTGTTCAGCCAGGTAGTGAGACTGCAGTTGCCATCCTGCGCT
TCTGCACAGCCCTGGGCTATGTCAACAGTTGTCTCAATCCCATTCTCTATGCTTTCCTGG
ATGAGAACTTCAAGGCCTGCTTTAGAAAGTTCTGCTGTGCTTCATCCCTGCACCGGGAGA
TGCAGGTTTCTGATCGTGTGCGGAGCATTGCCAAGGATGTTGGCCTTGGTTGCAAGACTT
CTGAGACAGTACCACGGCCAGCATGACTAGGCGTGGACCTGCCCATGGTGCCTGTCAGCC
CTGAACCTTGAGCATCTGGAGCC
```

FIG. 12

```
GTACTGAGTGGCTTTGCAGGGTGACAGCATGGAGTCCCTCTTTCCTGCTCCATACTGGGAGGTCT
TGTATGGCAGCCACTTTCAAGGGAACCTGTCCCTCCTAAATGAGACCGTACCCCACCACCTGCTC
CTCAATGCTAGTCACAGCGCCTTCCTGCCCCTTGGACTCAAGGTCACCATCGTGGGGCTCTACTT
GGCTGTGTGCATCGGGGGGCTCCTGGGGAACTGCCTCGTCATGTATGTCATCCTCAGCTGGGAGG
GCATTGAGGGGGACTGGAGACAGCAGGCACACCAAGATGAAGACAGCTACCAACATTTACATATT
TAATCTGGCACTGGCTGATACCCTGGTCTTGCTAACACTGCCCTTCCAGGGCACAGACATCCTAC
TGGGCTTCTGGCCATTTGGGAATGCACTCTGCAAGACTGTCATTGCTATCGACTACTACAACATG
TTTACCAGCACTTTTACTCTGACCGCCATGAGCGTAGACCGCTATGTGGCTATCTGCCACCCTAT
CCGTGCCCTTGATGTTCGGACATCCAGCAAAGCCCAGGCTGTTAATGTGGCCATATGGGCCCTGG
CTTCAGTGGTTGGTGTTCCTGTTGCCATCATGGGTTCAGCACAAGTGGAAGATGAAGAGATCGAG
TGCCTGGTGGAGATCCCTGCCCCTCAGGACTATTGGGGCCCTGTATTCGCCATCTGCATCTTCCT
TTTTTCCTTCATCATCCCTGTGCTGATCATCTCTGTCTGCTACAGCCTCATGATTCGACGACTTC
GTGGTGTCCGTCTGCTTTCAGGCTCCCGGGAGAAGGACCGAAACCTGCGGCGTATCACTCGACTG
GTGCTGGTAGTGGTGGCTGTGTTTGTGGGCTGCTGGACGCCTGTGCAGGTGTTTGTCCTGGTTCA
AGGACTGGGTGTTCAGCCAGGTAGTGAGACTGCAGTTGCCATCCTGCGCTTCTGCACAGCCCTGG
GCTATGTCAACAGTTGTCTCAATCCCATTCTCTATGCTTTCCTGGATGAGAACTTCAAGGCCTGC
TTTAGAAAGTTCTGCTGTGCTTCATCCCTGCACCGGGAGATGCAGGTTTCTGATCGTGTGCGGAG
CATTGCCAAGGATGTTGGCCTTGGTTGCAAGACTTCTGAGACAGTACCACGGCCAGCATGACTAG
GCGTGGACCTGCCCATGGTGCCTGTCAGCCCACAGAGCCCATCTACACCCAACACGGAGCTCACA
CAGGTCACTGCTCTCTAGGTTGACCCTGAACCTTGAGCATCTGGAGCC
```

FIG. 13

```
TTGCAGGGCAGTGGCATGGAGCCCCTCTTCCCCGCGCCGTTCTGGGAGGTTATCTACGGC
AGCCACCTTCAGGGCAACCTGTCCCTCCTGAGCCCCAACCACAGTCTGCTGCCCCCGCAT
CTGCTGCTCAATGCCAGCCACGGCGCCTTCCTGCCCCTCGGGCTCAAGGTCACCATCGTG
GGGCTCTACCTGGCCGTGTGTGTCGGAGGGCTCCTGGGGAACTGCCTTGTCATGTACGTC
ATCCTCAGGTAGGCTGGGCCCCAAGGTTCCTGTCTGGCACACCAAAATGAAGACAGCCAC
CAATATTTACATCTTTAACCTGGCCCTGGCCGACACTCTGGTCCTGCTGACGCTGCCCTT
CCAGGGCACGGACATCCTCCTGGGCTTCTGGCCGTTTGGGAATGCGCTGTGCAAGACAGT
CATTGCCATTGACTACTACAACATGTTCACCAGCACCTTCACCCTAACTGCCATGAGTGT
GGATCGCTATGTAGCCATCTGCCACCCCATCCGTGCCCTCGACGTCCGCACGTCCAGCAA
AGCCCAGGCTGTCAATGTGGCCATCTGGGCCCTGGCCTCTGTTGTCGGTGTTCCCGTTGC
CATCATGGGCTCGGCACAGGTCGAGGATGAAGAGATCGAGTGCCTGGTGGAGATCCCTAC
CCCTCAGGATTACTGGGGCCCGGTGTTTGCCATCTGCATCTTCCTCTTCTCCTTCATCGT
CCCCGTGCTCGTCATCTCTGTCTGCTACAGCCTCATGATCCGGCGGCTCCGTGGAGTCCG
CCTGCTCTCGGGCTCCCGAGAGAAGGACCGGAACCTGCGGCGCATCACTCGGCTGGTGCT
GGTGGTAGTGGCTGTGTTCGTGGGCTGCTGGACGCCTGTCCAGGTCTTCGTGCTGGCCCA
AGGGCTGGGGGTTCAGCCGAGCAGCGAGACTGCCGTGGCCATTCTGCGCTTCTGCACGGC
CCTGGGCTACGTCAACAGCTGCCTCAACCCCATCCTCTACGCCTTCCTGGATGAGAACTT
CAAGGCCTGCTTCCGCAAGTTCTGCTGTGCATCTGCCCTGCGCCGGGACGTGCAGGTGTC
TGACCGCGTGCGCAGCATTGCCAAGGACGTGGCCCTGGCCTGCAAGACCTCTGAGACGGT
ACCGCGGCCCGCATGACTAGGCGTGGACCTGCCCATG
```

FIG. 14

```
TTGCAGGGCAGTGGCATGGAGCCCCTCTTCCCCGCGCCGTTCTGGGAGGTTATCTACGGCAG
CCACCTTCAGGGCAACCTGTCCCTCCTGAGCCCCAACCACAGTCTGCTGCCCCCGCATCTGC
TGCTCAATGCCAGCCACGGCGCCTTCCTGCCCCTCGGGCTCAAGGTCACCATCGTGGGGCTC
TACCTGGCCGTGTGTGTCGGAGGGCTCCTGGGGAACTGCCTTGTCATGCACACCAAAATGAA
GACAGCCACCAATATTTACATCTTTAACCTGGCCCTGGCCGACACTCTGGTCCTGCTGACGC
TGCCCTTCCAGGGCACGGACATCCTCCTGGGCTTCTGGCCGTTTGGGAATGCGCTGTGCAAG
ACAGTCATTGCCATTGACTACTACAACATGTTCACCAGCACCTTCACCCTAACTGCCATGAG
TGTGGATCGCTATGTAGCCATCTGCCACCCCATCCGTGCCCTCGACGTCCGCACGTCCAGCA
AAGCCCAGGCTGTCAATGTGGCCATCTGGGCCCTGGCCTCTGTTGTCGGTGTTCCCGTTGCC
ATCATGGGCTCGGCACAGGTCGAGGATGAAGAGATCGAGTGCCTGGTGGAGATCCCTACCCC
TCAGGATTACTGGGGCCCGGTGTTTGCCATCTGCATCTTCCTCTTCTCCTTCATCGTCCCCG
TGCTCGTCATCTCTGTCTGCTACAGCCTCATGATCCGGCGGCTCCGTGGAGTCCGCCTGCTC
TCGGGCTCCCGAGAGAAGGACCGGAACCTGCGGCGCATCACTCGGCTGGTGCTGGTGGTAGT
GGCTGTGTTCGTGGGCTGCTGGACGCCTGTCCAGGTCTTCGTGCTGGCCCAAGGGCTGGGGG
TTCAGCCGAGCAGCGAGACTGCCGTGGCCATTCTGCGCTTCTGCACGGCCCTGGGCTACGTC
AACAGCTGCCTCAACCCCATCCTCTACGCCTTCCTGGATGAGAACTTCAAGGCCTGCTTCCG
CAAGTTCTGCTGTGCATCTGCCCTGCGCCGGGACGTGCAGGTGTCTGACCGCGTGCGCAGCA
TTGCCAAGGACGTGGCCCTGGCCTGCAAGACCTCTGAGACGGTACCGCGGCCCGCATGACTA
GGCGTGGACCTGCCCATG
```

FIG. 15

```
              10         20         30         40         50         60
mKOR 3D  MESLFPAPFWEVLYGSHFQGNLSLLNETV---PHHLLLNASHSAFLPLGLKVTIVGLYLAVCI
         :: ::::::::: :::: :::::::      : ::::::::: :::::::::::::::::::
hKOR 3D  MEPLFPAPFWEVIYGSHLQGNLSLLSPNHSLLPPHLLLNASHGAFLPLGLKVTIVGLYLAVCV
                                                           ‾‾‾‾‾‾‾‾‾‾‾

70         80         90        100        110        123
mKOR 3D  GGLLGNCLVMHTKMKTATNIYIFNLALADTLVLLTLPFQGTDILLGFWPFGNALCKTVIAIDY
         ::::::::::::::::::::::::::::::::::::::::::::::::::::::::::::::
hKOR 3D  GGLLGNCLVMHTKMKTATNIYIFNLALADTLVLLTLPFQGTDILLGFWPFGNALCKTVIAIDY
         ‾‾‾‾‾‾‾‾‾‾‾‾‾‾‾‾‾‾‾‾‾‾‾ ‾‾‾‾‾‾‾‾‾‾‾‾‾‾‾‾‾‾‾‾         ‾‾‾‾‾‾‾‾‾
                    I                     II 130        140        150        160        170        186
mKOR 3D  YNMFTSTFTLTAMSVDRYVAICHPIRALDVRTSSKAQAVNVAIWALASVVGVPVAIMGSAQVE
         ::::::::::::::::::::::::::::::::::::::::::::::::::::::::::::::
hKOR 3D  YNMFTSTFTLTAMSVDRYVAICHPIRALDVRTSSKAQAVNVAIWALASVVGVPVAIMGSAQVE
         ‾‾‾‾‾‾‾‾‾‾‾‾‾‾‾‾‾‾‾‾‾‾                   ‾‾‾‾‾‾‾‾‾‾‾‾‾‾‾‾‾‾‾‾
                    III                                   IV 190        200        210        220        230        249
mKOR 3D  DEEIECLVEIPAPQDYWGPVFAICIFLFSFIIPVLIISVCYSLMIRRLRGVRLLSGSREKDRN
         :::::::::: : ::::::::::::::::: :::::: :::::::::::::::::::::::
hKOR 3D  DEEIECLVEIPTPQDYWGPVFAICIFLFSFIVPVLVISVCYSLMIRRLRGVRLLSGSREKDRN
                       ‾‾‾‾‾‾‾‾‾‾‾‾‾‾‾‾‾‾‾‾‾‾‾‾‾‾‾‾‾
                                    V 260        270        280        290        300        313
mKOR 3D  LRRITRLVLVVVAVFVGCWTPVQVFVLVQGLGVQPGSETAVAILRFCTALGYVNSCLNPILYA
         ::::::::::::::::::::::::::::: :::::: :::::::::::::::::::::::::
hKOR 3D  LRRITRLVLVVVAVFVGCWTPVQVFVLAQGLGVQPSSETAVAILRFCTALGYVNSCLNPILYA
                ‾‾‾‾‾‾‾‾‾‾‾‾‾‾‾‾‾‾‾‾‾‾‾‾                ‾‾‾‾‾‾‾‾‾‾‾‾‾
                        VI                                     VII 320        330        340        350    363
mKOR 3D  FLDENFKACFRKFCCASALHREMQVSDRVRSIAKDVGLGCKTSETVPRPA
         :::::::::::::::::::::: : :::::::::::::: :::::::::
hKOR 3D  FLDENFKACFRKFCCASALRRDVQVSDRVRSIAKDVALACKTSETVPRPA   95% Identity
         ‾‾
```

FIG. 16

```
              10        20        30        40        50        60
mKOR 3A  MLATVPSCPLDSRSPSWGSTWLCASGGSWGTASSCMSSSAGRALRGTGDSRHTKMKTATN
         :: : ::::::::::::::::::::::::::::::::::::::::::::::::::::::::
rKOR 3A  MLVTAPSCPLDSRSPSWGSTWLCASGGSWGTASSCMSSSAGRALRGTGDSRHTKMKTATN
         :  :::::: :::::::::: : : :::::: :: ::: :: :     ::::::::::
hKOR 3A  MPATAPSCPSGSRSPSWGSTWPCVSEGSWGTALSCTSSS GR-LGPKVPVWHTKMKTATN
                                                       I 70        80        90       100       110       120
mKOR 3A  IYIFNLALADTLVLLTLPFQGTDILLGFWPFGNALCKTVIAIDYYNMFTSTFTLTAMSVD
         ::::::::::::::::::::::::::::::::::::::::::::::::::::::::::::
rKOR 3A  IYIFNLALADTLVLLTLPFQGTDILLGFWPFGNALCKTVIAIDYYNMFTSTFTLTAMSVD
         ::::::::::::::::::::::::::::::::::::::::::::::::::::::::::::
hKOR 3A  IYIFNLALADTLVLLTLPFQGTDILLGFWPFGNALCKTVIAIDYYNMFTSTFTLTAMSVD
             II                                III 130       140       150       160       170       180
mKOR 3A  RYVAICHPIRALDVRTSSKAQAVNVAIWALASVVGVPVAIMGSAQVEDEEIECLVEIPAP
         ::::::::::::::::::::::::::::::::::::::::::::::::::::::::::::
rKOR 3A  RYVAICHPIRALDVRTSSKAQAVNVAIWALASVVGVPVAIMGSAQVEDEEIECLVEIPAP
         ::::::::::::::::::::::::::::::::::::::::::::::::::::::::: :
hKOR 3A  RYVAICHPIRALDVRTSSKAQAVNVAIWALASVVGVPVAIMGSAQVEDEEIECLVEIPTP
                                         IV 190       200       210       220       230       240
mKOR 3A  QDYWGPVFAICIFLFSFIIPVLIISVCYSLMIRRLRGVRLLSGSREKDRNLRRITRLVLV
         ::::::::::::::::::::::::::::::::::::::::::::::::::::::::::::
rKOR 3A  QDYWGPVFAICIFLFSFIIPVLIISVCYSLMIRRLRGVRLLSGSREKDRNLRRITRLVLV
         ::::::::::::::::: ::: ::::::::::::::::::::::::::::::::::::::
hKOR 3A  QDYWGPVFAICIFLFSFIVPVLVISVCYSLMIRRLRGVRLLSGSREKDRNLRRITRLVLV
                     V 250       260       270       280       290       300
mKOR 3A  VVAVFVGCWTPVQVFVLVQGLGVQPGSETAVAILRFCTALGYVNSCLNPILYAFLDENFK
         ::::::::::::::::::::::::::::::::::::::::::::::::::::::::::::
rKOR 3A  VVAVFVGCWTPVQVFVLVQGLGVQPGSETAVAILRFCTALGYVNSCLNPILYAFLDENFK
         :::::::::::::::::: ::::::: :::::::::::::::::::::::::::::::::
hKOR 3A  VVAVFVGCWTPVQVFVLAQGLGVQPSSETAVAILRFCTALGYVNSCLNPILYAFLDENFK
              VI                                            VII 310       320       330       340
mKOR 3A  ACFRKFCCASALHREMQVSDRVRSIAKDVGLGCKTSETVPRPA
         :::::::::::: ::::::::::::::::::::::::::::::
rKOR 3A  ACFRKFCCASSLHREMQVSDRVRSIAKDVGLGCKTSETVPRPA          99% Identity
         :::::::::::: :  :::::::::::::::: :  ::::::
hKOR 3A  ACFRKFCCASALRRDVQVSDRVRSIAKDVALACKTSETVPRPA          91% Identity
```

```
        551       1a
         |        ⮕
...tccag CTGGGAGGGCATTGAGGGAACTGGAGACAGCAG gtgagga...
                                          |
                                         596
```

FIG. 18B

```
        2000                                                                          1c
         |                                                                             ⮕
..tGctag ACAACACATTGTGCACTTGGAAGATCTTTGATGAACTTTACAG GCAGTGCCCTGAAAACCCTCTGAGAGGA
                                                    |
                                                    1b ⮕

GTCTTAAGAGAGACTGAGGAGAGAAGACATCTCTCTCTTGATTCCTTCCACAAATTCACATTCAG gttaga...
                                                                  |
                                                                 2150
```

FIG. 18C

```
  1
  |
GTCAGTGGGCAGTCCTCCTCCCCTGACCAATCAGTTCCCCATGGTTCTTGCCGGCCCCCTGACCTCATTTCCTCCTGCAG
                                                                               |
                                                                              81
```

IDENTIFICATION AND CHARACTERIZATION OF MULTIPLE SPLICE VARIANTS OF THE KAPPA₃-RELATED OPIOID RECEPTOR (KOR-3) GENE

CROSS-REFERENCE TO RELATED APPLICATIONS

This is a National Phase Application of International Application No. PCT/US99/15977, having an international filing date of Jul. 15, 1999, and designating the U.S. and claiming priority from U.S. Application No. 60/093,002, filed Jun. 16, 1998.

STATEMENT OF RIGHTS TO INVENTIONS MADE UNDER FEDERALLY SPONSORED RESEARCH

This work was supported by the government, in part, by grants from the National Institute on Drug Abuse (DA 00296, DA 02615 and DA 000220) and a core grant from the National Cancer Institute (CA 08748). The government may have certain rights to this invention.

TECHNICAL FIELD

The present invention relates to kappa₃-related-opioid receptor-3 (KOR-3) splice variant polypeptides, to KOR-3 splice variant polynucleotides, to methods of screening compositions for agonists and antagonists of the splice variant receptor activities and to methods of measuring splice variant polypeptide binding activities.

BACKGROUND ART

Opiates are drugs derived from opium and include morphine, codeine and a wide variety of semisynthetic opioid congeners derived from them and from thebaine, another component of opium. Opioids include the opiates and all agonists and antagonists with morphine-like activity and naturally occurring endogenous and synthetic opioid peptides. Morphine and other morphine-like opioid agonists are commonly used pharmaceutically to produce analgesia.

There are now many compounds with pharmacological properties similar to those produced by morphine, but none has proven to be clinically superior in relieving pain. References to morphine herein will be understood to include morphine-like agonists as well. The effects of morphine on human beings are relatively diverse and include analgesia, drowsiness, changes in mood, respiratory depression, decreased gastrointestinal motility, nausea, vomiting, and alterations of the endocrine and autonomic nervous systems. Pasternak (1993) Clin. Neuropharmacol. 16:1. Doses of morphine need to be tailored based on individual sensitivity to the drug and the pain-sparing needs of the individual. For instance, the typical initial dose of morphine (10 mg/70 kg) relieves post-operative pain satisfactorily in only two-thirds of patients. Likewise, responses of an individual patient may vary dramatically with different morphine-like drugs and patients may have side effects with one such drug and not another. For example, it is known that some patients who are unable to tolerate morphine may have no problems with an equianalgesic dose of methadone. The mechanisms underlying variations in individual responses to morphine and morphine-like agonists have not been defined.

The analgesic effects of morphine are transduced through opioid receptors in the central nervous system (CNS), located at both spinal and multiple supraspinal sites. Morphine and other agonists induce profound analgesia when administered intrathecally or instilled locally into the dorsal horn of the spinal cord. Several mechanisms of action are believed to mediate the inhibition of nociceptive reflexes from reaching higher centers of the brain, including the inhibition of neurotransmitter release by opioid receptors on the termini of primary afferent nerves and post synaptic inhibitory actions on interneurons and on the out-put neurons of the spinothalamic tract.

Profound analgesia can also be produced by the instillation of morphine into the third ventricle or within various sites in the midbrain and medulla, most notably the periaqueductal gray matter, the nucleus raphe magnus, and the locus ceruleus. Although the neuronal circuitry responsible has not been defined, these actions produce enhanced activity in the descending aminergic bulbospinal pathways that exert inhibitory effects on the processing of nociceptive information in the spinal cord. Simultaneous administration of morphine at both spinal and supraspinal sites results in a synergized analgesic response, with a ten-fold reduction in the total dose of morphine necessary to produce equivalent analgesia at either site alone.

Morphine also exerts effects on the neuroendocrine system. Morphine acts in the hypothalamus to inhibit the release of gonadotropin releasing hormone (GnRH) and corticotropin-releasing factor (CRF), thus decreasing circulating concentrations of luteinizing hormone (LH), follicle stimulating hormone (FSH), and adrenocorticotropin (ACTH), and β-endorphin. As a result of the decreased concentrations of pituitary trophic hormones, the concentrations of testosterone and cortisol in the plasma decline. The administration of opiates increases the concentration of prolactin (PRL) in plasma, most likely by reducing the dopaminergic inhibition of PRL secretion. With chronic administration, tolerance eventually develops to the effects of morphine on hypothalamic releasing factors.

Opiates can interfere with normal gastrointestinal functioning. Morphine decreases both gastric motility and the secretion of hydrochloric acid in the stomach. Morphine may delay passage of gastric contents through the duodenum for as long as 12 hours. Morphine also decreases biliary, pancreatic, and intestinal secretions and delays the digestion of food in the small intestine. Propulsive peristaltic waves in the colon are diminished or abolished after administration of morphine and commonly, constipation occurs. For a detailed review of the physiologic effects of morphine, see Reisine and Pasternak (1996) Goodman & Gilman's The pharmacological basis of therapeutics, Ninth Edition (Hardman et al. eds.) McGraw-Hill pp 521–555.

Morphine also exerts effects on the immune system. The most firmly established effect of morphine is its ability to inhibit the formation of rosettes by human lymphocytes. The administration of morphine to animals causes suppression of the cytotoxic activity of natural killer cells and enhances the growth of implanted tumors. These effects appear to be mediated by actions within the CNS. By contrast, β-endorphin enhances the cytotoxic activity of human monocytes in vitro and increases the recruitment of precursor cells into the killer cell population; this peptide also can exert a potent chemotactic effect on these cells. A novel type of receptor (designated ε) may be involved. These effects, combined with the synthesis of proopiomelanocortin (POMC) and preproenkephalin by various cells of the immune system, have stimulated studies of the potential role of opioids in the regulation of immune function. Sibinga and Goldstein (1988) Annu. Rev. Immunol. 6:219.

Side effects resulting from the use of morphine range from mild to life-threatening. Morphine causes constriction of the pupil by an excitatory action on the parasympathetic nerve innervating the pupil. Morphine depresses the cough reflex through inhibitory effects on the cough centers in the medulla. Nausea and vomiting occur in some individuals through direct stimulation of the chemoreceptor trigger zone for emesis, in the postrema of the medulla. Therapeutic doses of morphine also result in peripheral vasodilatation, reduced peripheral resistance and an inhibition of baroreceptor reflexes in the cardiovascular system. Additionally, morphine provokes the release of histamines, which can cause hypotension. Morphine depresses respiration, at least in part by direct effects on the brainstem regulatory systems. In humans, death from morphine poisoning is nearly always due to respiratory arrest. Opioid antagonists can produce a dramatic reversal of severe respiratory depression and naloxone is currently the treatment of choice. High doses of morphine and related opioids can produce convulsions, which are not always relieved by anticonvulsant agents, such as naloxone.

The development of tolerance and physical dependence with repeated use is a characteristic feature of all opiates. Dependence seems to be closely related to tolerance, since treatments that block tolerance to morphine also block dependence. In vivo studies in animal models demonstrate the importance of neurotransmitters and their interactions with opioid pathways in the development of tolerance to morphine. Blockade of glutamate actions by noncompetitive and competitive NMDA (N-methyl-D-aspartate) antagonists blocks morphine tolerance. Trujillo and Akil (1991) Science 251:85; and Elliott et al. (1994) Pain 56:69. Blockade of the glycine regulatory site on NMDA receptors has similar effects to block tolerance. Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. U.S.A. 90:5162. These studies indicate several important aspects of tolerance and dependence. First, the selective actions of drugs on tolerance and dependence demonstrate that analgesia can be dissociated from these two unwanted actions. Second, the reversal of preexisting tolerance by NMDA antagonists and nitric oxide synthase inhibitors indicates that tolerance is a balance between activation of processes and reversal of those processes. These observations suggest that, by use of selective agonists or antagonists, tolerance and dependence in the clinical management of pain can be minimized or disassociated from the therapeutic effects.

In addition to morphine, there are a variety of opioids suitable for clinical use. These include, but are not limited to, Levorphanol, Meperidine, Fentanyl, Methadone, Codeine, Propoxyphene and various opioid peptides. Certain opioids are mixed agonists/antagonists and partial agonists. These include pentazocine, nalbuphine, butorphanol, and buprenorphine. The pharmacological effects of levorphanol closely parallel those of morphine although clinical reports suggest that levorphanol produces less nausea.

Meperidine exerts its chief pharmacological effects on the CNS and the neural elements in the bowel. Meperidine produces a pattern of effects similar but not identical to those described for morphine. In equianalgesic doses, meperidine produces as much sedation, respiratory depression, and euphoria as morphine. The pattern of unwanted side effects that follow the use of meperidine are similar to those observed after equianalgesic doses of morphine, except that constipation and urinary retention are less common.

Fentanyl is a synthetic opioid estimated to be 80 times as potent as morphine as an analgesic. High doses of fentanyl can result in severe toxicity and produce side effects including muscular rigidity and respiratory depression.

Methadone is an opioid with pharmacological properties similar to morphine. The properties of methadone include effective analgesic activity, efficacy by the oral route and persistent effects with repeated administration. Side effects include detection of miotic and respiratory-depressant effects for more than 24 hours after a single dose, and marked sedation is seen in some patients. Effects on cough, bowel motility, biliary tone and the secretion of pituitary hormones are qualitatively similar to those of morphine. In contrast to morphine, codeine is approximately 60% as effective orally as parenterally, both as an analgesic and as a respiratory depressant.

Codeine has an exceptionally low affinity for opioid receptors, and the analgesic effect of codeine is due to its conversion to morphine. However, codeine's antitussive actions probably involve distinct receptors that bind codeine specifically.

Propoxyphene produces analgesia and other CNS effects that are similar to those seen with morphine. It is likely that at equianalgesic doses the incidence of side effects such as nausea, anorexia, constipation, abdominal pain, and drowsiness would be similar to those of codeine.

Opioid antagonists have therapeutic utility in the treatment of overdosage with opioids. As understanding of the role of endogenous opioid systems in pathophysiologic states increases, additional therapeutic indications for these antagonists will emerge. If endogenous opioid systems have not been activated, the pharmacological actions of opioid antagonists depend on whether or not an opioid agonist has been administered previously, the pharmacological profile of that opioid and the degree to which physical dependence on an opioid has developed. The antagonist naloxone produces no discernible subjective effects aside from slight drowsiness. Naltrexone functions similarly, but with higher oral efficacy and a longer duration of action. Currently, naloxone and naltrexone are used clinically to treat opioid overdoses. Their potential utility in the treatment of shock, stroke, spinal cord and brain trauma, and other disorders that may involve mobilization of endogenous opioids remains to be established.

The complex interactions of morphine and drugs with mixed agonist/antagonist properties are mediated by multiple classes of opioid receptors. Opioid receptors comprise a family of cell surface proteins, which control a range of biological responses, including pain perception, modulation of affective behavior and motor control, autonomic nervous system regulation and neuroendocrinological function. There are three major classes of opioid receptors in the CNS, designated mu, kappa and delta, which differ in their affinity for various opioid ligands and in their cellular distribution. The different classes of opioid receptors are believed to serve different physiologic functions. Olson et al. (1989) Peptides 10:1253; Lutz and Pfister (1992) J. Receptor Res. 12:267; and Simon (1991) Medicinal Res. Rev. 11:357. Morphine produces analgesia primarily through the mu-opioid receptor. However, among the opioid receptors, there is substantial overlap of function as well as of cellular distribution.

Members of each known class of opioid receptor have been cloned from human cDNA and their predicted amino acid sequences have been determined. Yasuda et al. (1993) Proc. Natl. Acad. Sci. U.S.A. 90:6736; and Chen et al. (1993) Mol. Pharmacol. 44:8. The opioid receptors belong to a class of transmembrane spanning receptors known as G-protein coupled receptors. G-proteins consist of three tightly associated subunits, alpha, beta and gamma (1:1:1) in order of decreasing mass. Following agonist binding to the receptor, a conformational change is transmitted to the G-protein, which causes the G-alpha subunit to exchange a bound GDP for GTP and to dissociate from the beta and gamma subunits. The GTP-bound form of the alpha subunit is typically the effector-modulating moiety. Signal amplification results from the ability of a single receptor to activate many G-protein molecules, and from the stimulation by G-alpha-GTP of many catalytic cycles of the effector.

Most opioid receptor-mediated functions appear to be mediated through G-protein interactions. Standifer and Pasternak (1997) Cell Signal. 9:237. Antisense oligodeoxynucleotides directed against various G-protein alpha subunits were shown to differentially block the analgesic actions of the mu-, delta-, and kappa-opioid-agonists in mice. Standifer et al. (1996) Mol. Pharmacol. 50:293.

The amino acid sequences of the opioid receptors are approximately 65% identical, and they have little sequence similarity to other G-protein-coupled receptors except for somatostatin. Reisine and Bell (1993) Trends Neurosci. 16:506. The regions of highest similarity in sequence are the sequences predicted to lie in the seven transmembrane-spanning regions and the intracellular loops. Regions of amino acid sequence divergence are the amino and carboxy termini and the second and third extracellular loops.

Each receptor subtype has a characteristic pattern of expression. Mu-opioid receptor mRNA is present in the periaqueductal gray, spinal trigeminal nucleus, cuneate and gracile nuclei, and thalamus regions of the brain involved in pain perception and associated with morphine analgesia (Defts et al. (1994) J. Comp. Neurol. 345:46); in nuclei involved in control of respiration, consistent with the ability of morphine to depress respiration; and in neurons of the area postrema, where morphine has been shown to cause nausea and induce vomiting. Other consequences of mu-opioid receptor activation include miosis, reduced gastrointestinal motility, and feelings of well-being or euphoria. Pasternak (1993). The pattern of mu-opioid receptor mRNA expression correlates with the brain centers involved in mediating the biological actions of morphine and mu-selective agonists. Delta-opioid receptor mRNA is found in the dorsal horn of the spinal cord. $Kappa_1$-opioid receptor mRNA is expressed in the hypothalamic regions, which may account for many of the neuroendocrine effects of the kappa selective agonists.

Alternative splicing has been observed with a number of G-protein-coupled receptors, including somatostatin 2 (Vanetti et al. (1998) FEBS Lett. 311:290), dopamine D2 (Guiramand et al. (1995) J. Biol. Chem. 270:7354), prostaglandin EP3 (Namba et al. (1993) Trends Pharmacol. Sci. 16:246), serotonin receptor subtypes $5-HT_4$ and $5-HT_7$ (Lucas and Hen. (1995) Trends Pharmacol. Sci. 16:246) and KOR-3. Bare et al. (1994) FEBS Lett. 354:213; and Zimprich et al. (1995) FEBS Lett. 359:142.

Several opioid receptor splice variants have been identified and characterized. At least two MOR-1 splice variants are known, the human MOR-1A and the rat MOR-1BI Bare et al. (1994); and Zimprich et al. (1995). The hMOR-1A splice variant consists of exons 1, 2, 3 and a new exon 3a, and was determined to possess ligand binding characteristics similar to the full-length MOR-1. Bare et al. (1994).

In the case of the Kappa-opioid receptor, few variants have been found. This member of the opioid receptor family was cloned from human (ORL-1; hereinafter hKOR-3), mouse (KOR-3; hereinafter mKOR-3) and other species. U.S. Pat. No. 5,747,279; Bunzow et al. (1994) FEBS Lett. 347:284–288; Fukuda et al. (1994) FEBS Lett. 343:42–46; Wick et al. (1994) Molec. Brain Res. 27:37–44; Pan et al. (1996) Gene 171:255–260; Mollereau et al. (1994) FEBS Lett. 341:33–38; and Pan et al. (1995) Mol. Pharmacol. 47:1180–1188.

The structure of mouse KOR-3 gene has been defined as having five exons separated by four introns. Pan et al. (1996). Although structurally homologous with the cloned traditional opioid receptors, mKOR-3 has low affinity for most opioids and opioid peptides. The ligand for KOR-3 has been identified and designated orphanin FQ/nociceptin (OFQ/N). Reinscheid et al. (1995) Science 270:792–794; and Meunier et al. (1995) Nature 377:532–535. OFQ/N is intimately involved with pain perception, but its actions are complex. Initially, it was reported to be hyperalgesic and that low doses reverse the actions of opioids. Reinscheid et al. (1995); Meunier et al. (1995); Mogil et al. (1996) Neurosci. Lett. 214:1–4; Mogil et al. (1996) Neurosci. 75:333–337; Grisel et al. (1996) NeuroReport 7:2125–2129; Tian et al. (1997) Pharmacol. 120:676–680; Zhu et al. (1997) Neurosci. Lett. 235:37–40; and King et al. (1998) Biochem. Pharmacol. 55:1537–1540. Yet OFQ/N is also an analgesic. Tian (1997); Rossi et al. (1997) J. Pharmacol. Exp. Ther. 282:858–865; Rossi et al. (1996) Eur. J. Pharmacol. 31:R7–R8; King et al. (1997) Neurosci. Lett. 223:113–116; and Yamamoto et al. (1997) Neurosci. 81:249–254.

The complex pharmacology of OFQ/N and antisense studies of KOR-3 raised the possibility of multiple OFQ/N receptors. Rossi et al. (1997); Rossi et al. (1996); King et al. (1997); Mathis et al. (1997) Biochem. Biophys. Res. Commun. 230:462–465; and Pan et al. (1995). Radiolabeled OFQ/N binding to brain homogenates is quite distinct from that to the cloned receptor and is consistent with binding site heterogeneity in the brain. Mathis et al. (1997); Reinscheid et al. (1995); and Pan et al. (1996) FEBS Lett. 395:207–210. Antisense mapping of the three coding exons of the receptor encoded by KOR-3 also raised the question of alternative splicing. Pan et al. (1994) Regul. Pept. 54:217–218; Pan et al. (1995); Rossi et al. (1997); Rossi et al. (1997); and Pasternak et al. (1995) Trends Pharmacol. Sci. 16:344–350. Antisense probes targeting the first coding exon blocked OFQ/N hyperalgesia, but not analgesia, whole other probes targeting the second and third exons blocked analgesia and not hyperalgesia. The second and third coding exons, but not the first, also have been implicated in $kappa_3$ analgesia. These observations raised the possibility that the $kappa_3$ receptor and KOR-3 might result from alternative splicing of the same gene. Pan et al. (1996).

Two alternative splice KOR variants have been reported, including a rat variant (XOR1L) which contains a 28 amino acid residue insertion between 15 base deletion corresponding to Tyr71-Arg75 in the first intracellular loop. Wang et al. (1994) FEBS Lett 1994 348:75–79; and Halford et al. (1995) J. Neuroimmunol. 59:91–101.

Availability of polynucleotide sequences encoding opioid receptor splice variants, and the corresponding polypeptide sequences, will significantly increase the capability to design pharmaceutical compositions, such as analgesics, with enhanced specificity of function. In general, the availability of these polypeptide sequences will enable efficient screening of candidate compositions. The principle in operation through the screening process is straightforward: natural agonists and antagonists bind to cell-surface receptors and channels to produce physiologic effects; certain other molecules can produce physiologic effects and act as therapeutic pharmaceutical agents. Thus, the ability of candidate drugs to bind to opioid receptor splice variants can function as an extremely effective screening criterion for the selection of pharmaceutical compositions with a desired functional efficacy and specificity.

DISCLOSURE OF THE INVENTION

The invention encompasses KOR-3 splice variant polypeptides.

The invention further encompasses a KOR-3 splice variant polynucleotide, including those encoding KOR-3 splice variant polypeptides.

The invention further encompasses methods of screening compositions for an opioid activity by obtaining a control cell that does not express a recombinant or endogenous opioid receptor, obtaining a test cell that expresses a recombinant KOR-3 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further encompasses methods of screening compositions for an opioid activity by obtaining a control polypeptide that is not a recombinant opioid receptor, obtaining a test polypeptide that is a recombinant KOR-3 splice variant polypeptide, contacting a composition with the control polypeptide and the test polypeptide, contacting the test polypeptide with an amount of an opioid sufficient to measurably bind the test polypeptide, measuring the binding of the composition and the opioid, and comparing the test polypeptide binding of the composition to that of the opioid, where determination of binding of the composition is expressed relative to that of the opioid.

The invention further encompasses methods of screening compositions for differential opioid activity comprising obtaining a first and second test polypeptide that are KOR-3 splice variant polypeptides and contacting each with a composition, measuring the binding affinity of the composition to the first and second test polypeptides and comparing the binding of the composition and the first test polypeptide to that of the second test polypeptide where differential activity is expressed as a ratio of the two binding affinities.

The invention further encompasses a non-human animal in which one or both endogenous KOR-3 alleles has been altered by homologous recombination with an exogenously introduced nucleic acid provided herein.

The invention further encompasses a non-human transgenic animal carrying a transgene comprising a KOR-3 splice variant polynucleotide.

The invention further encompasses a method for regulating morphine analgesia in a subject by altering the amount of KOR-3 polypeptide activity. Activity can be regulated by administering antigen binding fragments, agonists, antagonists or small molecule ligands to a subject in an amount of and a duration sufficient to regulate morphine analgesia. The antigen binding fragment, agonist, antagonist or small molecule ligand is directed to an KOR-3 splice variant polypeptide.

Opioid activity can also be regulated by administering a DNA plasmid vector containing a KOR-3 splice variant polynucleotide. The DNA plasmid vector thereby expresses an KOR-3 polynucleotide in a subject in an amount of and a duration sufficient to regulate morphine analgesia. Activity can also be regulated by administering an antisense nucleic acid complementary to a KOR-3 splice variant polynucleotide, thereby blocking gene expression in a subject in an amount of and a duration sufficient to regulate morphine analgesia.

The invention further encompasses a method for regulating body weight in a subject by altering the amount of KOR-3 polypeptide activity. Activity can be regulated by administering antigen binding fragments, agonists, antagonists or small molecule ligands to a subject in an amount of and a duration sufficient to regulate body weight. The antigen binding fragment, agonist, antagonist or small molecule ligand is directed to an KOR-3 splice variant polypeptide.

Activity can also be regulated by administering a DNA plasmid vector containing a KOR-3 splice variant polynucleotide. The DNA plasmid vector thereby expresses an KOR-3 polynucleotide in a subject in an amount of and a duration sufficient to regulate body weight. Activity can also be regulated by administering an antisense nucleic acid complementary to a KOR-3 splice variant polynucleotide, thereby blocking gene expression in a subject in an amount of and a duration sufficient to regulate body weight.

The invention further encompasses a method for diagnosing an KOR-3 splice variant-associated pharmacological abnormality, comprising measuring the amount of variant activity or tissue distribution thereof in a subject and comparing that activity or tissue distribution to a control sample, wherein a difference in the amount of activity or tissue distribution correlates with the presence of a pharmacological defect.

The invention further encompasses a method for diagnosing an KOR-3 splice variant-associated disorder of the neuroendocrine system, comprising measuring the amount of variant activity or tissue distribution thereof in a subject and comparing that activity or tissue distribution to a control sample, wherein a difference in the amount of activity or tissue distribution correlates with the presence of a disorder of the neuroendocrine system.

The invention further encompasses antigen-binding fragments specific for the KOR-3 splice variants described herein.

BRIEF DESCRIPTION OF THE DRAWINGS

FIG. 2 is the amino acid (AA) sequence specific to mKOR-3A (exons 1,1a,2,3) and the GenBank accession number.

FIG. 3 is the AA sequence specific to mKOR-3B (exons, 1,1b) and the GenBank accession number.

FIG. 4 is the AA sequence specific to mKOR-3C (exons, 1,1c) and the GenBank accession number.

FIG. 5 is the AA sequence specific to mKOR-3E (exons 1,2,2a).

FIG. 6 is the AA sequence specific to rKOR-3A (exons 1,1a,2,3).

FIG. 7 is the AA sequence specific to hKOR-3A (exons 1,1a, 2, 3).

FIG. 8 is the AA sequence specific to hKOR 3D (exons 1a, 2, 3).

FIGS. 9A and 9B is the nucleic acid sequence specific to mKOR-3A (exons 1,1a,2,3) and the GenBank accession number.

FIG. 10 is the nucleic acid sequence mKOR-3B (exons 1,2,1b,3,4) and the GenBank accession number.

FIGS. 11A and 11B is the nucleic acid sequence mKOR-3C (exons 1,2,1c,3,4,5) and the GenBank accession number.

FIG. 12 is the nucleic acid sequence of mKOR-3E (exons 1,2,3,2a,4).

FIG. 13 is the nucleic acid sequence specific to rKOR-3A (exons 1,1a,2,3).

FIG. 14 is the nucleic acid sequence of hKOR-3A (exons 1,1a,2,3).

FIG. 15 is the nucleic acid sequence hKOR-3D (exons 1a,2,3).

FIG. 16 is the amino acid alignment of mKOR-3D and hKOR-3D. Dots indicate identities in the sequences; differences are indicated by the indicated residues. Underlined sequences are putative transmembrane regions.

FIG. 17 is the amino acid alignment of mKOR-A, rKOR-3A and hKOR-3A. Dots indicate identities in the sequences; differences are indicated by the indicated residues. Bold sequences indicate the predicted amino acid sequence from coding exon 1 and insertion sequences. Underlined sequences are putative transmembrane sequences.

FIG. 18 is the insertion sequences of KOR-3, A, B, C and E. Insertion sequences of (a) KOR-3A, (b) KOR-3B and KOR-3C, (c) KOR-3E. Intronic sequences are in lower case and exons are in upper case. Base numbers for genomic and cDNA sequences are based upon intron 2 of the KOR-3 gene (GenBank accession number U32939) and KOR-3 cDNA (GenBank accession number U09421) sequences. The splice junctions are indicated by arrows. In (b) arrows indicate the splice junctions for KOR-3c and KOR-b.

BEST MODE FOR CARRYING OUT THE INVENTION

Figure 1:
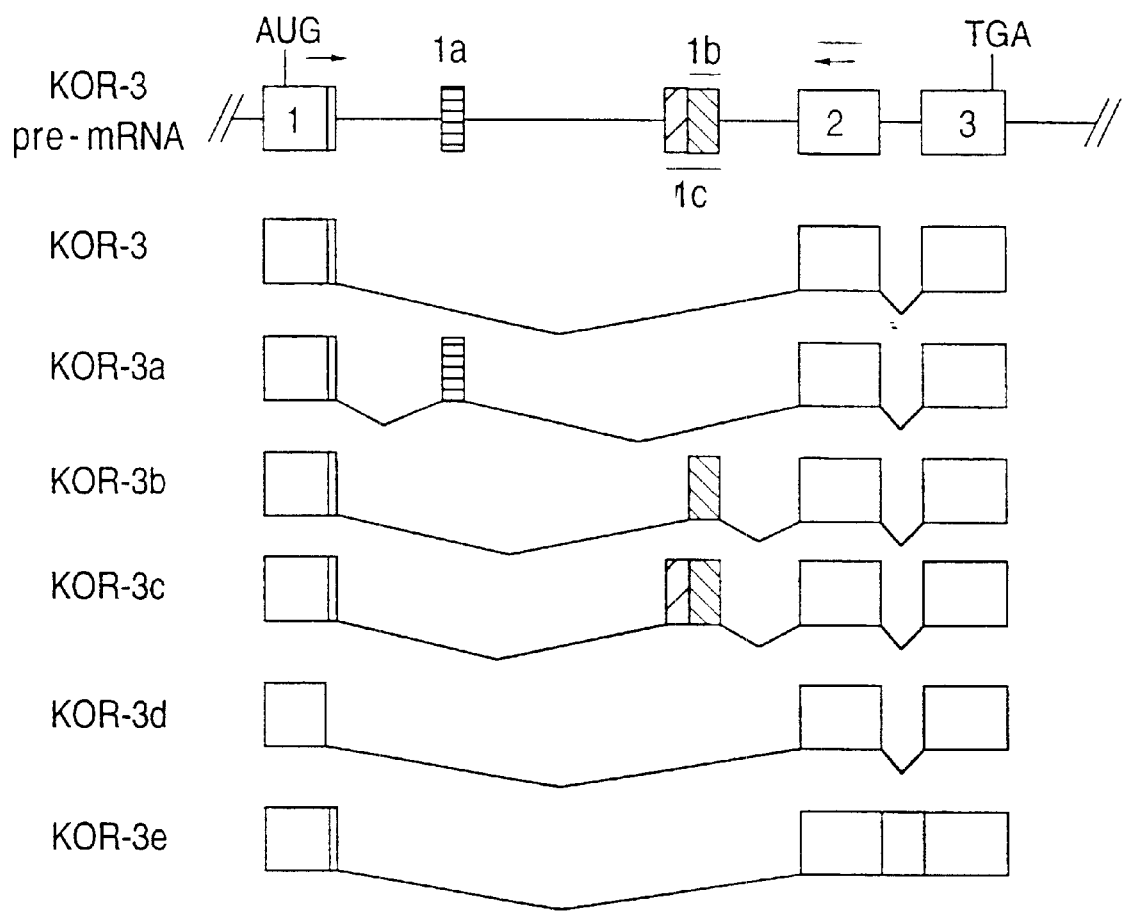
FIG. 1 is a schematic diagram of KOR-3 genes and alternative splicing. Exons and introns are indicated by open boxes and horizontal lines, respectively. Mini-exon 1c (34 bp) is shown by the solid box with horizontal lines, mini-exon 1b (98 bp) by the solid box with diagonal lines and mini-exon 1c (139 bp) (including mini-exon 1b) by a solid black box and box 1b. The shaded area of exon 1 represents the deletion originally reported in lymphocytes by Halford et al. (1995) which has also now been found in brain. Arrows represent the primers used in RT-PCR to clone the splice variants. The short heavy line over exon 3 denotes the probe used in Southern blotting to detect expression of KOR-3 gene splicing variants.

SEQ ID NOS: are assigned to the sequences as described below:

SEQ ID NO: 1 refers to the amino acid sequence of mouse KOR3A

SEQ ID NO: 2 refers to the amino acid sequence of mouse KOR3B

SEQ ID NO: 3 refers to the amino acid sequence of mouse KOR3C

SEQ ID NO: 4 refers to the amino acid sequence of mouse KOR3E

SEQ ID NO: 5 refers to the amino acid sequence of rat KOR3A

SEQ ID NO: 6 refers to the amino acid sequence of human KOR3A

SEQ ID NO: 7 refers to the amino acid sequence of human KOR3D

SEQ ID NO: 8 refers to the nucleotide sequence of mouse KOR3a

SEQ ID NO: 9 refers to the nucleotide sequence of mouse KOR3b

SEQ ID NO: 10 refers to the nucleotide sequence of mouse KOR3c

SEQ ID NO: 11 refers to the nucleotide sequence of mouse KOR3e

SEQ ID NO: 12 refers to the nucleotide sequence of rat KOR3a

SEQ ID NO: 13 refers to the nucleotide sequence of human KOR3a

SEQ ID NO: 14 refers to the nucleotide sequence of human KOR3d

SEQ ID NO: 15 refers to the nucleotide sequence of mouse KOR-3D

SEQ ID NO: 16 refers to the nucleotide insertion sequence of mouse KOR-3A

SEQ ID NO: 17 refers to the nucleotide insertion sequence of mouse KOR-3B

SEQ ID NO: 18 refers to the nucleotide insertion sequence of mouse KOR-3E

SEQ ID NO: 19 refers to the amino acid sequence of the basic unit of linking peptide (GGGGS)

SEQ ID NO: 20 refers to the nucleotide sequence of sense primer (5'-TGCCTTCCTGCCCCTTGGAC-3')

SEQ ID NO: 21 refers to the nucleotide sequence of anti-sense primer (5'-CCCAGAAGGATGTCTGTGCCC-3')

SEQ ID NO: 22 refers to the nucleotide sequence of probe (5'-GGTGTGCCTGCTGTCTCCAGTTCCCCTCAA TGCCCTCCCAGCTGAGGA-3')

SEQ ID NO: 23 refers to the nucleotide sequence of probe (5'-CCTCAGTCTCTCTTAAGACTCTCAGAGGG TTTTCAGGGCACTGCC-3')

SEQ ID NO: 24 refers to the nucleotide sequence of sense primer (5'-TCCTGGGGAACTGCCTCGTC-3')

SEQ ID NO: 25 refers to the nucleotide sequence of anti-sense primer (5'-CCCAGAAGGATGTCTGTGCCC-3')

SEQ ID NO: 26 refers to the nucleotide insertion sequence of mouse KOR-3C

This invention encompasses splice variants of the KOR-3 gene exemplified by newly isolated KOR-3 splice variant polypeptides. The exemplary KOR-3 splice variant polypeptides are composed of the amino acids indicated in FIGS. 2–8. Polypeptides comprising 5 amino acids, more preferably 7 amino acids, more preferably 15 amino acids, more preferably 25 amino acids, more preferably 50 amino acids and more preferably 75 amino acids, which are not the same as known variants are also included. The exemplary KOR-3 splice variant polypeptides retain KOR-3 activity. The complete cDNA sequences of KOR-3A, KOR-3B, and KOR-3C have been deposited in GenBank, numbers AF043276, AF043277, and AF043278 respectively, in satisfaction of the requirements of the Budapest Treaty.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation of modification, such as conjugation with a labeling or bioactive component.

The KOR-3 splice variant polypeptides, including polypeptide fragments, homologs thereof, retain KOR-3 activity. To "retain KOR-3 activity" is to have a similar level of functional activity as the KOR-3 polypeptide. This activity includes but is not limited to, immunologic and pharmacological activity.

The "immunologic activity" is binding to anti-opioid receptor antigen binding fragments. The antigen binding fragments can be whole native antibodies, bispecific antibodies, chimeric antibodies, Fab, F(ab')2, single chain V region fragments (scFv), and fusion polypeptides comprising an antigen binding fragment fused to a chemically functional moiety.

The "pharmacologic activity" is activation or deactivation of the KOR-3 splice variant polypeptides upon binding of agonists or antagonists.

The invention further encompasses KOR-3 splice variant polypeptide homologs. A "homolog" is a polypeptide similar in amino acid sequence to other polypeptides among a single species or, a "homolog" in evolution is a polypeptide similar in amino acid sequence to other polypeptides in different species because they have been inherited from a common ancestor. Preferably, homologs of the present invention are human homologs.

Isolation of KOR-3 splice variant human homolog cDNAs can be carried out by any method known in the art. For instance, methods analogous to the isolation of the mouse KOR-3 splice variants described herein (see Example 1). Using primers corresponding to the human KOR-3 gene and a Marathon-Ready human cDNA Library to carry out reactions according to the Marathon cDNA Amplification Kit (Clontech), human KOR-3 splice variants can be obtained. Alternatively, screening of human cDNA libraries with probes corresponding to mouse KOR-3 splice variant sequences can be carried out at reduced stringency to identify human KOR-3 splice variant cDNAs.

The invention further encompasses the KOR-3 splice variant polypeptides in a heterodimeric or homodimeric form. A "heterodimer" is a protein made up of more than one kind of polypeptide. A "homodimer" is a protein made up of more than one kind of polypeptide.

The invention further encompasses isolated KOR-3 splice variant polynucleotide sequences indicated in FIGS. 9–15 and 18. In addition to these, the polynucleotide sequence can be any sequence of the appropriate genetic code to encode any of the KOR-3 splice variant polypeptides indicated in FIGS. 2–8, 16 and 17. Preferably, the polynucleotide is at least 15 consecutive nucleotides.

A "polynucleotide" or "nucleic acid" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, MRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, preferably at least 70%, more preferably at least 80%, and even more preferably at least 90% free of these materials.

The invention further comprises a complementary strand to the polynucleotide encoding the KOR-3 splice variant polypeptide.

The complementary strand may be a polymeric form of nucleotides of any length, which contain deoxyribonucleotides, ribonucleotides, and analogs in any combination.

Hybridization reactions can be performed under conditions of different "stringency". Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the KOR-3 splice variant polypeptides and functionally equivalent fragments thereof which may enhance, decrease or not significantly affect properties of the polypeptides encoded thereby. These functionally equivalent variants, derivatives, and fragments display the ability to retain KOR-3 activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutanine; aspartic acid/glutamic acid; serine/threonine/methionine; lysine/arginine; and phenylalanine/tyrosine/tryptophan.

The invention further encompasses the KOR-3 splice variant polynucleotide sequences contained in a vector molecule or an expression vector and operably linked to a promoter element if necessary.

A "vector" refers to a recombinant DNA or RNA plasmid or virus that comprises a heterologous polynucleotide to be delivered to a target cell, either in vitro or in vivo. The heterologous polynucleotide can comprise a sequence of interest for purposes of therapy, and can be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides or nucleic acids of the invention can comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell, and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, or it can be obtained directly from the DNA by using a DNA-dependent RNA polymerase.

Expression vectors generally are replicable polynucleotide constructs that contain a polynucleotide encoding the polypeptide of interest. Herein, this means any of the KOR-3 splice variant polypeptides. For expression, one or more translational controlling elements are also usually required, such as ribosome binding sites, translation initiation sites and stop codons. These controlling elements (transcriptional and translational) can be derived from the KOR-3 gene, or heterologous (i.e., derived from other genes or other organisms). A number of expression vectors suitable for expression in eukaryotic cells including yeast, avian, and mammalian cells are well known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of an KOR-3 splice variant polypeptide of interest. Another example of an expression vector system is the baculovirus/insect system.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available for complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and other cloning vectors are available from commercial vendors such as BioRad, Stratagene, and Invitrogen.

The invention further encompasses non-human animals in which one or both KOR-3 alleles has been altered by homologous recombination with an exogenously introduced nucleic acid.

Non-human animals devoid of one or more gene products are generated to determine the "loss-of-function" phenotype associated with the loss of that particular gene product. Herein, the gene product is the KOR-3 gene or splice variants thereof. Phenotypic abnormalities can be present, for instance, in anatomical structures, biochemical and genetic pathways and pharmacological responses. Loss-of-function phenotypic analysis has the potential to reveal the function of the gene product.

Methods of homologous recombination with an exogenously introduced nucleic acid are used to inactivate one or more alleles in non-human animals. These methods, as applied to mice and rats, are well known in the art. Capecchi (1989) Science 244:1288. Usually, an exogenous polynucleotide encoding a selectable marker gene, and having sufficient sequence homology to the targeted site of integration at either end of the polynucleotide, is introduced into the genome of embryonic stem cells (ES cells) derived from the inner cell mass of non-human animal blastocysts. Evans and Kaufman (1981) Nature 292:154. Through homologous recombination, the polynucleotide is incorporated into the genetic locus at the targeted site of integration, replacing the corresponding sequences of the endogenous allele. ES cells are used to generate chimeric animals either by microinjection into, or aggregation with wildtype embryos. Chimeric animals having germ line transmission of the inactivated allele are bred to produce heterozygous, and subsequently, homozygous lines carrying the inactivated allele. Robertson (1991) Biol. Reprod. 44:238.

The invention further encompasses non-human transgenic animals carrying a transgene encoding an KOR-3 splice variant polypeptide.

Non-human animals carrying additional copies of the gene of interest are generated to determine the "gain-of-function" phenotype associated with excess of that particular gene product. Herein, the gene product is any of the KOR-3 gene splice variants. Phenotypic abnormalities can be present, for instance, in anatomical structures, biochemical and genetic pathways and pharmacological responses. Gain-of-function phenotypic analysis has the potential to reveal the function of the gene product.

Methods of generating transgenic animals are well known in the art. Jaenisch (1988) Science 240:1468. "Transgenes" are exogenous polynucleotides encoding the gene of interest. Transgenes are introduced into the embryonic genome through microinjection. Alternatively, a transgene encoding the gene of interest and a selectable marker gene is introduced into the ES cell genome through transfection or electroporation. ES cells carrying the transgene are subsequently used to produce animals with multiple copies of the gene of interest.

Pharmaceutical compositions and treatment modalities can be detected by the methods of this invention. The KOR-3 splice variant polypeptides and corresponding nucleic acid sequences can be used in screening for compositions that alter variant activity. Compositions that selectively regulate the KOR-3 splice variant polypeptides or selectively modulate physiologic processes can be identified.

The invention further encompasses methods of screening compositions for opioid activity by obtaining a control cell that does not express a recombinant opioid receptor and obtaining a test cell that is the same as the control cell except that it expresses a recombinant KOR-3 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further comprises a method of screening compositions for opioid activity by obtaining a control polypeptide that is not a recombinant opioid receptor and obtaining a test polypeptide that is a recombinant KOR-3 splice variant polypeptide, contacting a composition with the control polypeptide and the test polypeptide, contacting the test polypeptide with an amount of an opioid sufficient to measurably bind the test polypeptide, measuring the binding of the composition and the opioid and comparing the test polypeptide binding of the composition to that of the opioid, where determination of binding of the composition is expressed relative to that of the opioid.

The invention further encompasses a method of screening compositions for differential opioid activity by obtaining a first test polypeptide that is a KOR-3 splice variant polypeptide, and contacting it with a composition and obtaining a second test polypeptide that is an KOR-3 splice variant polypeptide, measuring the binding of the composition to the first and second test polypeptides, and comparing the binding of the composition and the first test polypeptide to that of the second test polypeptide where differential activity is expressed as a ratio of the two binding affinities.

The compositions screened include but are not limited to chemical, synthetic combinatorial libraries of small molecule ligands, eukaryotic whole cell lysates or extracts, media conditioned by cultured eukaryotic cells, natural products and extracts thereof.

The opioid can be but is not limited to, morphine, etorphine, levorphanol, [D-Ala$^2$, MePhe$^4$, Gly(ol)$^5$] enkephalin (DAMGO), pentazocine, nalbuphine, naloxone benzoylhydrazone, ethylketocyclazocine, bremazocine and analogs thereof.

The physiologic effect can be measured by any method known in the art such as changes in the levels of neuroendocrine hormones including but not limited to prolactin, growth hormone, gonadotropin-releasing hormone, adrenocorticotropin, corticotropin-releasing factor, luteinizing hormone, follicle stimulating hormone, testosterone or cortisol.

The physiologic effect is also measured by changes in the levels of neurotransmitters, including but not limited to, acetylcholine or dopamine.

Activation of the KOR-3 receptor, and likely, the KOR-3 splice variant polypeptides, stimulates a variety of physiologic responses, including analgesia, depression of gastrointestinal motility and respiration, and alterations of the endocrine and autonomic nervous system. Compositions that regulate the activity of the KOR-3 receptor and/or the KOR-3 splice variant polypeptides can elicit responses that have therapeutic effects. The invention is useful in diagnosis, treatment, design and screening of novel reagents.

The invention further encompasses a method for regulating morphine analgesia in a subject by altering the amount of KOR-3 polypeptide activity in the subject. Activity can be regulated by administering antigen binding fragments, agonists, antagonists or small molecule ligands to a subject in an amount and a duration sufficient to regulate morphine analgesia. The antigen binding fragment, agonist, antagonist or small molecule ligand is directed to an KOR-3 splice variant polypeptide.

Activity can also be regulated by administering a DNA plasmid vector containing a KOR-3 splice variant polynucleotide. The DNA plasmid vector thereby expresses an KOR-3 polypeptide in a subject in an amount and a duration sufficient to regulate morphine analgesia. Activity can also be regulated by administering an antisense nucleic acid complementary to a KOR-3 splice variant polynucleotide, thereby blocking gene expression in a subject in an amount and a duration sufficient to regulate morphine analgesia.

The invention further encompasses a method for regulating body weight in a subject by altering the amount of KOR-3 polypeptide activity. Activity can be regulated by administering antigen binding fragments, agonists, antagonists or small molecule ligands to a subject in an amount and a duration sufficient to regulate body weight. The antigen binding fragment, agonist, antagonist or small molecule ligand is directed to a KOR-3 splice variant polypeptide.

Activity can also be regulated by administering a DNA plasmid vector containing a KOR-3 splice variant polynucleotide. The DNA plasmid vector thereby expresses a KOR-3 polynucleotide in a subject in an amount of and a duration sufficient to body weight. Activity can also be regulated by administering an antisense nucleic acid complementary to a KOR-3 splice variant polynucleotide, thereby blocking gene expression in a subject in an amount and a duration sufficient to regulate body weight.

Agonists and antagonists of KOR-3 splice variant activity can include but are not limited to, morphine, methadone, etorphine, levorphanol, fentanyl, sufentanil, [D-Ala$^2$, MePhe$^4$, Gly(ol)5]enkephalin (DAMGO), butorphanol, naloxone, naltrexone, D-Phe-Cys-Tyr-D-Trp-Orn-Thr-Pen- Thr-NH$_2$ (CTOP), diprenorphine, β-funaltrexamine, naloxonazine, nalorphine, pentazocine, nalbuphine, benzoylhydrazone, bremazocine, ethylketocyclazocine, U50488, U69593, spiradoline, naltrindole, [D-Pen$^2$, D-Pen$^5$]enkephalin (DPDPE), [D-Ala$^2$,Glu$^4$]deltorphin, [D-Ser$^2$, Leu$^5$]enkephalin-Thr$^6$ (DSLET), Met-enkephalin, Leu-enkephalin, β-endorphin, dynorphin A, dynorphin B, α-neoendorphin.

A "subject" is a vertebrate, preferably a mammal, and more preferably a human. Mammals include but are not limited to humans, farm animals, sport animals, and pets.

The invention further encompasses a method for diagnosing a KOR-3 splice variant-associated pharmacological abnormality, comprising measuring the amount of variant activity or tissue distribution thereof in a subject and comparing that activity or tissue distribution to a control sample, wherein a difference in the amount of activity or tissue distribution correlates with the presence of a pharmacological defect. This disorder can be heritable.

The invention further encompasses a method for diagnosing a KOR-3 splice variant-associated disorder of the neuroendocrine system, comprising measuring the amount of variant activity or tissue distribution thereof in a subject and comparing that activity or tissue distribution to a control sample, wherein a difference in the amount of activity or tissue distribution correlates with the presence of a disorder of the neuroendocrine system. This disorder can be heritable.

The invention further encompasses methods for generating antigen binding fragments specific for a KOR-3 splice variant polypeptide. According to the invention, a KOR-3 splice variant polypeptide can be used as an immunogen to generate antigen binding fragments which immunospecifically bind the immunogen.

Production of antigen binding fragments such as polyclonal antibodies may be carried out by any method known in the art. Various host animals can be immunized by injection with the immunogen, including but not limited to rabbits, mice and rats. Various adjuvants can be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and Corynebacterium parvum.

For preparation of antigen binding fragments such as monoclonal antibodies, any technique which provides for the production of antibody molecules by continuous cell lines in culture can be used. Examples of such techniques include the original hybridoma technique (Kohler and Milstein (1975) Nature 256:495) as well as the trioma technique, the human B-cell hybridoma technique (Kozbor et al. (1983) Immunol. Today 4:72), and the EBV hybridoma technique to produce human monoclonal antibodies (Cole et al. (1985) in Monoclonal Antibodies and Cancer Therapy, Alan R. Liss, Inc., pp. 77–96). Monoclonal antibodies can also be produced in germ-free animals utilizing recent technology (PCT/US90/02545). Human antibodies can be obtained using human hybridomas (Cote et al. (1983) Proc. Natl. Acad. Sci. U.S.A. 80:2026), or by transforming human B cells with EBV virus in vitro (Cole et al. (1985) in Monoclonal Antibodies and Cancer Therapy, Alan R. Liss, Inc., pp. 77–96). Techniques developed for the production of "chimeric antibodies" (Morrison et al. (1984) Proc. Natl. Acad. Sci. U.S.A. 81:6851; Neuberger et al. (1984) Nature 312:604; and Takeda et al. (1985) Nature 314:452) by splicing the genes from a mouse antibody molecule specific for KOR-3 splice variants together with genes from a human antibody of appropriate bioligical activity can be used.

Techniques described for the production of single chain antibodies (U.S. Pat. No. 4,946,778) can be adapted to produce KOR-3 splice variant-specific single chain antibodies. Techniques described for the production of Fab expression libraries (Huse et al. (1989) Science 246:1275) can be utilized, allowing rapid and easy identification of monoclonal Fab fragments specific for a KOR-3 splice variant polypeptide.

Antibody fragments which contain the idiotype of the molecule can be generated by known techniques. For example, such fragments include but are not limited to: the F(abl), fragment which can be produced by pepsin digestion of the antibody molecule; the Fab' fragments which can be generated by reducing the disulfide bridges of the F(abl) fragment, the Fab fragments which can be generated by treating the antibody molecule with papain and a reducing agent, and Fv fragments.

Single chain V region fragments ("scFv") can also be produced. Single chain V region fragments are made by linking L (light) and/or H (heavy) chain V (variable) regions by using a short linking peptide. Bird et al. (1988) Science 242:423. Any peptide having sufficient flexibility and length can be used as a linker in a scFv. Usually the linker is selected to have little to no immunogenicity. An example of a linking peptide is (GGGGS)$_3$ SEQ ID NO: 19, which bridges approximately 3.5 nm between the carboxy terminus of one V region and the amino terminus of another V region. Other linker sequences can also be used, and can provide additional functions, such as a means for attaching a drug or a solid support.

All or any portion of the H or L chain can be used in any combination. Typically, the entire V regions are included in the scFv. For instance, the L chain V region can be linked to the H chain V region. Alternatively, a portion of the L chain V region can be linked to the H chain V region, or a portion thereof. Also contemplated are scFvs in which the H chain V region is from H11, and the L chain V region is from another immunoglobulin. It is also possible to construct a biphasic, scFv in which one component is a KOR-3 splice variant polypeptide and another component is a different polypeptide, such as a T cell epitope.

The scFvs can be assembled in any order, for example, $V_H$-(linker)-$V_L$ or $V_L$-(linker)-$V_H$. There may be a difference in the level of expression of these two configurations in particular expression systems, in which case one of these forms may be preferred. Tandem scFvs can also be made, such as (X)-(linker)-(X)-(linker)-(X), in which X are KOR-3 splice variant polypeptides, or combinations of KOR-3 splice variant polypeptides with other polypeptides. In another embodiment, single chain antibody polypeptides have no linker polypeptide, or just a short, inflexible linker. Exemplary configurations include $V_L$-$V_H$ and $V_H$-$V_L$. The linkage is too short to permit interaction between $V_L$ and $V_H$ within the chain, and the chains form homodimers with a $V_L$/$V_H$ antigen binding site at each end. Such molecules are referred to in the art as "diabodies".

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli,* and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

Expression conditions should ensure that the scFv assumes functional and, preferably, optimal tertiary structure. Depending on the plasmid used (especially the activity of the promoter) and the host cell, it may be necessary to modulate the rate of production. For instance, use of a weaker promoter, or expression at lower temperatures, may be necessary to optimize production of properly folded scFv in prokaryotic systems; or, it may be preferably to express scFv in eukaryotic cells.

The following examples are provided to illustrate but not limit the claimed invention.

EXAMPLE 1

Materials and Methods
Identification of Alternative Splicing Variants by RT-PCR

A sense (5'-TGCC TTC CTG CCC CTT GGA C-3'; positions 419–438) SEQ ID NO: 20 and an antisense primer (5'-CCC AGA AGG ATG TCT GTG CCC-3'; position 610–630) SEQ ID NO: 21 based upon the nucleotide sequence of the mouse KOR-3 clone (GenBank accession number U09621) were used to amplify cDNA fragments using PCR. The template was first-strand cDNA reverse transcribed with random hexameters from C57BL/6 mouse brain total RNA prepared as described by Chomczynski et al. (1987) Anal. Biochem. 162:156–159. Multiple bands were obtained by PCR, isolated, subcloned and sequenced in both directions. Four KOR-3-related clones were identified.
cDNA library screening A C57BL/6 mouse brain λZAP cDNA library was screened with a $^{32}$P-labeled 1.1 kb fragment containing the full length KOR-3 coding region at high stringency, identifying 32 positives. Three contained a 34 bp insertion (KOR-3a), one had a 98 bp insertion (KOR-3b), one had a 139 bp insertion (KOR-3c) and another had an 81 bp insertion between coding exons 2 and 3 (KOR-3e). KOR-3a and KOR-3c clones of approximately 2.9 kb and a 1.2 kb clone of KOR-3b were sequenced. Clones with the 15 bp deletion in the first exon in these screens were not observed.
Northern blot analysis Polyadenylated RNAs were isolated from mouse total RNAs using oligo(dT) chromatography (Pharmacia, Piscataway, N.J.) as described by Pan et al. (1995) Mol. Pharmacol. 47:1180–1188. Northern blotting followed the protocol for GeneScreen Plus membranes (New England Nuclear, Boston, Mass.). Probes for KOR-3a (5'-GGT GTG CCT GCT GTC TCC AGT TCC CCT CAA TGC CCT CCC AGC TGA GGA-3') SEQ ID NO: 22 and KOR-3b/KOR-3c (5'-CCT CAG TCT CTC TTA AGA CTC TCA GAG GGT TTT CAG GGC ACT GCC-3') SEQ ID NO: 23 were 5'-end $^{32}$P-labeled by T4 polynucleotide kinase. A $^{32}$P-labeled 1.1 kb fragment containing the full length of the KOR-3 coding region was generated by PCR with appropriate primers.

Total RNAs from various C57BL/6 mouse brain regions were extracted and reverse transcribed using random hexameters. Two primers were designed from the nucleotide sequence of mouse KOR-3/ORL-1 receptor at positions 486–505 (sense primer. 5'-TCC TGG GGA ACT GCC TCG TC-3') SEQ ID NO: 24 and 610–630 (antisense primer, 5'-CCC AGA AGG ATG TCT GTG CCC-3') SEQ ID NO: 25 and used in sequential PCR reactions with the first-strand cDNAs as templates. The predicted sizes of the amplified cDNA fragments for KOR-3, KOR-3a, KOR-3b and KOR-3c are 145 bp, 179 bp, 232 bp and 284 bp, respectively. The PCR products were then separated by 1.5% agarose gel, transferred on GeneScreen Plus membranes and hybridized with a $^{32}$P-labeled 107 bp fragment of the coding exon 2 generated.

EXAMPLE 2

Results
cDNA cloning of Alternative Splicing Variants of KOR-3 Gene

To look for variants differing in the region between the first and second coding exons, RT-PCR was performed using an upstream primer in the first coding exon and a downstream primer in the second. This led to the identification of four splice variants. Three had insertions between the first and second coding exons (FIG. 1) while the fourth had a 15 bp deletion at the 3'-end of the first coding exon, corresponding to a variant cloned from lymphocytes. Halford et al (1995).

Full length cDNAs were then isolated containing the 34 bp (KOR-3a), the 98 bp (KOR-3b) and the 139 bp (KOR-3c) insertions by screening a mouse brain cDNA library with a full length KOR-3 probe. The sequences of the new cDNAs were identical to that of the KOR-3 cDNA except for the insertions. The nucleotide sequences obtained and the corresponding amino acid residues encoded thereby are depicted in FIGS. 2–15. These sequences include human and rat homologs obtained by screening the relevant cDNA libraries and subsequent cloning.

Figure 19:
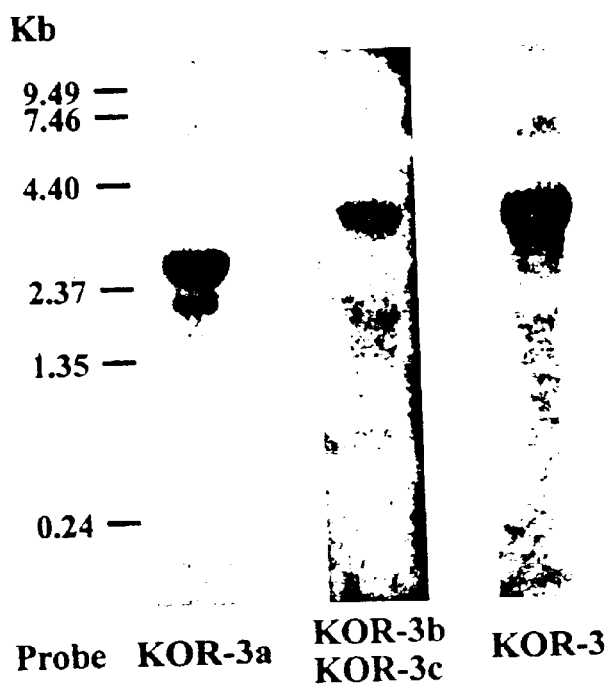
FIG. 19 is a Northern blot depicting KOR-3 and its splice variants. The probes used are indicated in the figure.
Figure 20:
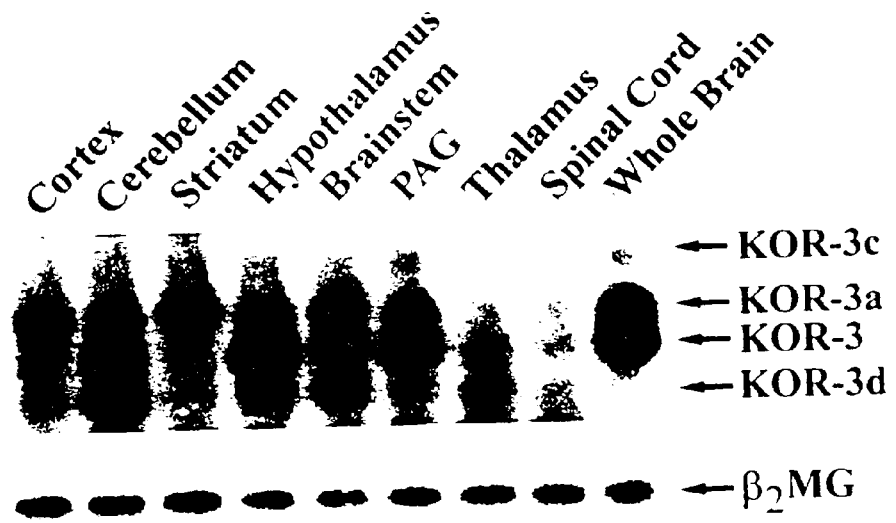
FIG. 20 is a Southern blot depicting the regional distribution of KOR-3 splice variants (KOR-3c, KOR-3a, KOR-3 and KOR-3d) in cortex, cerebellum, striatum, hypothalamus, brain stem, PAG, thalamus, spinal cord and whole brain.

Comparison of mKOR-3D and hKOR-3D are provided in FIG. 16, while mKOR-3A, rKOR-3A and hKOR-3A are compared in FIG. 17. The insertion sequences of KOR-3a, KOR-3b and KOR-3c were aligned to the intron between the first and second coding exons of the KOR-3 gene (Pan et al (1996)) and the 81 bp insertion in KOR-3e to the intron between the second and third coding exons (FIG. 18). All of the splice sites were in agreement with the GT/AG rule.
Northern analysis of KOR-3 and its splice variants Northern blot analysis was then used to investigate the full length transcripts of the variants obtained from whole brain mRNAs (FIG. 19). The KOR-3a probe hybridized a major transcript with a size of approximately 2.9 kb, with another smaller sized band of lower abundance. Since the 139 bp insertion in KOR-3c contains the 98 bp in KOR-3b, there is no specific probe for the KOR-3b. A 48 bp probe derived from the 98 bp was used to detect both the KOR-3b and KOR-3c expression. This probe hybridized a major transcript with a size of approximately 3.4 kb, which was similar to that probed by the KOR-3b probe. The relative abundance of the transcripts revealed by the KOR-3a probe was much higher than that by the KOR-3b and the KOR-3c probe, although it was less abundant than that by the KOR-3 probe. Bands with the KOR-3e probe were not visible.
Regional Expression of the Splice Variants The regional distribution of the variants using RT-PCR and Southern blotting was next examined. Four major bands were obtained with different intensities among the various regions (FIG. 20). The sizes of the four bands from the lower to the higher matched those of the 15 bp deletion (clone D), KOR-3, 34 bp insertion (clone A) and 139 bp insertion (clone C), respectively. To confirm that the amplified bands correspond to the KOR-3 splice variants, each band was extracted form the agarose gel, subcloned into the Bluescript vector and sequenced. In all cases, the sequences of the bands were identical to those of the variant clones. The relative abundance in whole brain of KOR-3 and its variants was similar to that seen with Northern blotting: KOR-3>KOR-3a>KOR-3c. Although KOR-3b expression was not seen in the initial PCR and the blotting, the KOR-3b fragment was amplified by a second round PCR using the gel extracts corresponding to the KOR-3b from the first PCR as templates. This implies a very low level of expression of KOR-3b in brain.

Among the regions examined, the KOR-3 transcript was most abundant in the hypothalamus and periaqueductal gray (PAG), while the cortex, striatum and brainstem had higher levels of the KOR-3a. The KOR-3c was highly expressed in PAG and hypothalamus and the KOR-3d in cerebellum, hypothalamus and brainstem. Lower levels of KOR-3c were seen in the cortex, PAG and thalamus. Interestingly, the only major variant expressed in the striatum was KOR-3a. This differential expression of the variants among the regions implies region-specific splicing.

EXAMPLE 3

Discussion

In addition to the variants reported earlier, we have now identified a number of additional splice variants of KOR-3/ORL-1. The insertions observed in the new variants correspond to the region between TM1 and the first intracellular loop, a splice site common among all the opioid receptors. Similar splicing variants with insertions between exons one and two have been identified in mouse delta receptors (DOR-1) gene (Gavereiaux-Ruff et al. (1997) Mol. Brain Res. 48:298–304) and the mu (MOR-1) gene. The presence of such a large number of variants underscores the extensive alternative splicing at this location. The splicing becomes even more interesting in view of the differential regional expression of these variants. Perhaps the best example is the striatum, which has been reported to be devoid of ORL-1 message and OFQ/N receptors. Little evidence was found for any appreciable levels of KOR-3/ORL-1 in this region, in contrast to the high expression of KOR-3a.

Identification of multiple KOR-3 variants with insertions between the first and second coding exons implies extensive alternative splicing at this location. G triplet repeats may play a role in exon-intron border selection and in alternative exon determination (McCullough et al. (1997) Mol. Cell. Biol. 17:4562–4571) and the 34 bp insertion sequence in KOR-3a contains three G triplets. Although the role of the G triplets within the 34 bp in KOR-3a splicing has not been established, it may be interesting to determine whether specific factors capable of binding the G triplets are differentially expressed among brain regions. It has also been reported that many alternatively spliced exons contain GAR repeats, where R is a purine, which have been referred to as exonic splicing enhancers of ESEs. Nagel et al. (1998) RNA 4:11–23. SRp55 is a specific ESE binding protein. Thus, the presence of multiple GAR repeats in the insertion sequences of both the KOR-3b and the KOR-3c might contribute to the regional expression of the KOR-3b and the KOR-3c.

The KOR-3e appears to be an intron-retention variant and is similar to a rat variant. Wang et al. (1994) FEBS Lett. 348:75–79. Unlike the murine version, which contains a termination codon which would lead to a truncated receptor lacking the last three transmembrane regions, the published rat version does not appear to have the termination codon.

Translation of the cDNAs using the start codon AUG of KOR-3 results in early termination either at the mini-exon insertion (KOR-3c) or shortly after the insertion (KOR-3a and KOR-3b). Yet, in preliminary studies the expressed full length clones containing these insertions bind the kappa$_3$ ligand [$^3$H]naloxone benzolhydrazone quite well. Although the truncated protein may retain high affinity for the ligands, this seems unlikely.

All references cited herein, are hereby incorporated herein. Although the foregoing invention has been described in some detail, by way of illustration and example for the purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. An isolated human KOR-3A splice variant polypeptide that consists essentially of the amino acid residues depicted in SEQ ID NO: 6.

2. An isolated heterodimeric or homodimeric complex comprising the polypeptide of claim 1.

3. An isolated polynucleotide, or an antisense strand that is fully complementary thereto, wherein the polynucleotide consists essentially of a human KOR-3A splice variant as depicted in SEQ ID NO: 13.

4. The polynucleotide of claim 3, wherein the polynucleotide is a DNA molecule.

5. The polynucleotide of claim 3, wherein the polynucleotide is an RNA molecule.

6. The polynucleotide of claim 3, wherein the polynucleotide is a DNA molecule comprising a nucleotide base sequence of SEQ ID NO: 13.

7. An expression vector comprising a polynucleotide that encodes a human KOR-3A splice variant polypeptide comprising an amino acid residue sequence of sequence SEQ ID NO: 6.

8. The expression vector of claim 7, wherein said polynucleotide is a DNA molecule comprising a nucleotide base sequence of SEQ ID NO: 13.

9. An expression vector comprising a polynucleotide that encodes a human KOR-3A splice variant polypeptide, wherein the vector comprises the nucleotide base sequence of sequence SEQ ID NO: 13.

10. The expression vector of claim 9, wherein the nucleotide base sequence of sequence SEQ ID NO: 13 is operatively linked to an enhancer and/or promoter.

11. A transformed host cell comprising a polynucleotide that encodes a human KOR-3A splice variant polypeptide, wherein the polynucleotide comprises the nucleotide base sequence of SEQ ID NO: 13.

12. The transformed host cell of claim 11, wherein the polynucleotide is introduced into the cell by transfection, electroporation or transformation of the cell with a vector comprising the polynucleotide.

13. The transformed host cell of claim 12, wherein the host cell expresses the polynucleotide to produce the encoded human KOR-3A splice variant polypeptide.

14. A process for preparing a transformed host cell expressing a human KOR-3A splice variant polypeptide comprising the steps of:

a) transfecting, electroporating or transforming a cell with a polynucleotide that encodes a human KOR-3 splice variant polypeptide comprising an amino acid residue sequence of SEQ ID NO: 6 to produce a transformed host cell; and b) maintaining the transformed host cell under biological conditions sufficient for expression of said human KOR-3A splice variant polypeptide in the host cell.

15. The process of claim 14, wherein the polynucleotide comprises a nucleotide base sequence of SEQ ID NO: 13.

16. A process for preparing a transformed host cell expressing a human KOR-3A splice variant polypeptide comprising the steps of:

a) transfecting, electroporating or transforming a cell with a polynucleotide that encodes a human KOR-3A splice variant polypeptide, wherein the polynucleotide is a DNA molecule comprising a nucleotide base sequence of SEQ ID NO: 13, to produce a transformed host cell; and b) maintaining the transformed host cell under biological conditions sufficient for expression of said a human KOR-3A splice variant polypeptide in the host cell.

17. A method of preparing a human KOR-3A splice variant polypeptide comprising expressing the polynucleotide of claim 6.

* * * * *

UNITED STATES PATENT AND TRADEMARK OFFICE
CERTIFICATE OF CORRECTION

PATENT NO. : 6,627,734 B1
DATED : September 30, 2003
INVENTOR(S) : Pasternak et al.

It is certified that error appears in the above-identified patent and that said Letters Patent is hereby corrected as shown below:

<u>Title page,</u>
Item [57], ABSTRACT,
Line 2, change "the muopioid receptor-1 (KOR-3)" to -- the kappa$_3$-related-opioid receptor-3 (KOR-3) --.

Signed and Sealed this

Twentieth Day of April, 2004

JON W. DUDAS
*Acting Director of the United States Patent and Trademark Office*

SEQUENCE LISTING

<160> NUMBER OF SEQ ID NOS: 26

<210> SEQ ID NO 1
<211> LENGTH: 343
<212> TYPE: PRT
<213> ORGANISM: mus musculus

<400> SEQUENCE: 1

```
Met Leu Ala Thr Val Pro Ser Cys Pro Leu Asp Ser Arg Ser Pro Ser
1               5                   10                  15

Trp Gly Ser Thr Trp Leu Cys Ala Ser Gly Gly Ser Trp Gly Thr Ala
            20                  25                  30

Ser Ser Cys Met Ser Ser Ser Ala Gly Arg Ala Leu Arg Gly Thr Gly
        35                  40                  45

Asp Ser Arg His Thr Lys Met Lys Thr Ala Thr Asn Ile Tyr Ile Phe
    50                  55                  60

Asn Leu Ala Leu Ala Asp Thr Leu Val Leu Leu Thr Leu Pro Phe Gln
65                  70                  75                  80
```

```
Gly Thr Asp Ile Leu Leu Gly Phe Trp Pro Phe Gly Asn Ala Leu Cys
                85                  90                  95

Lys Thr Val Ile Ala Ile Asp Tyr Tyr Asn Met Phe Thr Ser Thr Phe
            100                 105                 110

Thr Leu Thr Ala Met Ser Val Asp Arg Tyr Val Ala Ile Cys His Pro
        115                 120                 125

Ile Arg Ala Leu Asp Val Arg Thr Ser Lys Ala Gln Ala Val Asn
    130                 135                 140

Val Ala Ile Trp Ala Leu Ala Ser Val Val Gly Val Pro Val Ala Ile
145                 150                 155                 160

Met Gly Ser Ala Gln Val Glu Asp Glu Ile Glu Cys Leu Val Glu
                165                 170                 175

Ile Pro Ala Pro Gln Asp Tyr Trp Gly Pro Val Phe Ala Ile Cys Ile
                180                 185                 190

Phe Leu Phe Ser Phe Ile Ile Pro Val Leu Ile Ile Ser Val Cys Tyr
            195                 200                 205

Ser Leu Met Ile Arg Arg Leu Arg Gly Val Arg Leu Leu Ser Gly Ser
            210                 215                 220

Arg Glu Lys Asp Arg Asn Leu Arg Arg Ile Thr Arg Leu Val Leu Val
225                 230                 235                 240

Val Val Ala Val Phe Val Gly Cys Trp Thr Pro Val Gln Val Phe Val
                245                 250                 255

Leu Val Gln Gly Leu Gly Val Gln Pro Gly Ser Glu Thr Ala Val Ala
            260                 265                 270

Ile Leu Arg Phe Cys Thr Ala Leu Gly Tyr Val Asn Ser Cys Leu Asn
            275                 280                 285

Pro Ile Leu Tyr Ala Phe Leu Asp Glu Asn Phe Lys Ala Cys Phe Arg
            290                 295                 300

Lys Phe Cys Cys Ala Ser Ala Leu His Arg Glu Met Gln Val Ser Asp
305                 310                 315                 320

Arg Val Arg Ser Ile Ala Lys Asp Val Gly Leu Gly Cys Lys Thr Ser
                325                 330                 335

Glu Thr Val Pro Arg Pro Ala
            340

<210> SEQ ID NO 2
<211> LENGTH: 111
<212> TYPE: PRT
<213> ORGANISM: mus musculus

<400> SEQUENCE: 2

Met Glu Ser Leu Phe Pro Ala Pro Phe Trp Glu Val Leu Tyr Gly Ser
1               5                   10                  15

His Phe Gln Gly Asn Leu Ser Leu Leu Asn Glu Thr Val Pro His His
                20                  25                  30

Leu Leu Leu Asn Ala Ser His Ser Ala Phe Leu Pro Leu Gly Leu Lys
            35                  40                  45

Val Thr Ile Val Gly Leu Tyr Leu Ala Val Cys Ile Gly Gly Leu Leu
        50                  55                  60

Gly Asn Cys Leu Val Met Tyr Val Ile Leu Arg Gln Cys Pro Glu Asn
65                  70                  75                  80

Pro Leu Arg Gly Val Leu Arg Glu Thr Glu Glu Arg Gln His Leu
                85                  90                  95

Ser Leu Leu Ile Pro Ser Thr Asn Ser His Ser Gly Thr Pro Arg
```

<210> SEQ ID NO 3
<211> LENGTH: 95
<212> TYPE: PRT
<213> ORGANISM: mus musculus

<400> SEQUENCE: 3

```
Met Glu Ser Leu Phe Pro Ala Pro Phe Trp Glu Val Leu Tyr Gly Ser
1               5                   10                  15
His Phe Gln Gly Asn Leu Ser Leu Leu Asn Glu Thr Val Pro His His
                20                  25                  30
Leu Leu Leu Asn Ala Ser His Ser Ala Phe Leu Pro Leu Gly Leu Lys
            35                  40                  45
Val Thr Ile Val Gly Leu Tyr Leu Ala Val Cys Ile Gly Gly Leu Leu
        50                  55                  60
Gly Asn Cys Leu Val Met Tyr Val Ile Leu Arg Gln His Cys Ala Leu
65                  70                  75                  80
Gly Arg Ser Leu Met Asn Phe Thr Gly Ser Ala Leu Lys Thr Leu
                85                  90                  95
```

<210> SEQ ID NO 4
<211> LENGTH: 393
<212> TYPE: PRT
<213> ORGANISM: mus musculus

<400> SEQUENCE: 4

```
Met Glu Ser Leu Phe Pro Ala Pro Phe Trp Glu Val Leu Tyr Gly Ser
1               5                   10                  15
His Phe Gln Gly Asn Leu Ser Leu Leu Asn Glu Thr Val Pro His His
                20                  25                  30
Leu Leu Leu Asn Ala Ser His Ser Ala Phe Leu Pro Leu Gly Leu Lys
            35                  40                  45
Val Thr Ile Val Gly Leu Tyr Leu Ala Val Cys Ile Gly Gly Leu Leu
        50                  55                  60
Gly Asn Cys Leu Val Met Tyr Val Ile Leu Arg His Thr Lys Met Lys
65                  70                  75                  80
Thr Ala Thr Asn Ile Tyr Ile Phe Asn Leu Ala Leu Ala Asp Thr Leu
                85                  90                  95
Val Leu Leu Thr Leu Pro Phe Gln Gly Thr Asp Ile Leu Leu Gly Phe
            100                 105                 110
Trp Pro Phe Gly Asn Ala Leu Cys Lys Thr Val Ile Ala Ile Asp Tyr
            115                 120                 125
Tyr Asn Met Phe Thr Ser Thr Phe Thr Leu Thr Ala Met Ser Val Asp
        130                 135                 140
Arg Tyr Val Ala Ile Cys His Pro Ile Arg Ala Leu Asp Val Arg Thr
145                 150                 155                 160
Ser Ser Lys Ala Gln Ala Val Asn Val Ala Ile Trp Ala Leu Ala Ser
                165                 170                 175
Val Val Gly Val Pro Val Ala Ile Met Gly Ser Ala Gln Val Glu Asp
            180                 185                 190
Glu Gly Gln Trp Ala Val Leu Leu Pro Asp Gln Ser Val Pro His Gly
        195                 200                 205
Ser Cys Arg Pro Leu Pro His Phe Ser Pro Ala Glu Ile Glu Cys Leu
    210                 215                 220
Val Glu Ile Pro Ala Pro Gln Asp Tyr Trp Gly Pro Val Phe Ala Ile
```

```
225                 230                 235                 240
Cys Ile Phe Leu Phe Ser Phe Ile Ile Pro Val Leu Ile Ile Ser Val
                245                 250                 255
Cys Tyr Ser Leu Met Ile Arg Arg Leu Arg Gly Val Arg Leu Leu Ser
                260                 265                 270
Gly Ser Arg Glu Lys Asp Arg Asn Leu Arg Arg Ile Thr Arg Leu Val
                275                 280                 285
Leu Val Val Val Ala Val Phe Val Gly Cys Trp Thr Pro Val Gln Val
                290                 295                 300
Phe Val Leu Val Gln Gly Leu Gly Val Gln Pro Gly Ser Glu Thr Ala
305                 310                 315                 320
Val Ala Ile Leu Arg Phe Cys Thr Ala Leu Gly Tyr Val Asn Ser Cys
                325                 330                 335
Leu Asn Pro Ile Leu Tyr Ala Phe Leu Asp Glu Asn Phe Lys Ala Cys
                340                 345                 350
Phe Arg Lys Phe Cys Cys Ala Ser Ala Leu His Arg Glu Met Gln Val
                355                 360                 365
Ser Asp Arg Val Arg Ser Ile Ala Lys Asp Val Gly Leu Gly Cys Lys
                370                 375                 380
Thr Ser Glu Thr Val Pro Arg Pro Ala
385                 390

<210> SEQ ID NO 5
<211> LENGTH: 343
<212> TYPE: PRT
<213> ORGANISM: Rattus sp.

<400> SEQUENCE: 5

Met Leu Val Thr Ala Pro Ser Cys Pro Leu Asp Ser Arg Ser Pro Ser
1                 5                  10                  15
Trp Gly Ser Thr Trp Leu Cys Ala Ser Gly Gly Ser Trp Gly Thr Ala
                20                  25                  30
Ser Ser Cys Met Ser Ser Ser Ala Gly Arg Ala Leu Arg Gly Thr Gly
                35                  40                  45
Asp Ser Arg His Thr Lys Met Lys Thr Ala Thr Asn Ile Tyr Ile Phe
            50                  55                  60
Asn Leu Ala Leu Ala Asp Thr Leu Val Leu Leu Thr Leu Pro Phe Gln
65                  70                  75                  80
Gly Thr Asp Ile Leu Leu Gly Phe Trp Pro Phe Gly Asn Ala Leu Cys
                85                  90                  95
Lys Thr Val Ile Ala Ile Asp Tyr Tyr Asn Met Phe Thr Ser Thr Phe
                100                 105                 110
Thr Leu Thr Ala Met Ser Val Asp Arg Tyr Val Ala Ile Cys His Pro
                115                 120                 125
Ile Arg Ala Leu Asp Val Arg Thr Ser Ser Lys Ala Gln Ala Val Asn
130                 135                 140
Val Ala Ile Trp Ala Leu Ala Ser Val Val Gly Val Pro Val Ala Ile
145                 150                 155                 160
Met Gly Ser Ala Gln Val Glu Asp Glu Glu Ile Glu Cys Leu Val Glu
                165                 170                 175
Ile Pro Ala Pro Gln Asp Tyr Trp Gly Pro Val Phe Ala Ile Cys Ile
                180                 185                 190
Phe Leu Phe Ser Phe Ile Ile Pro Val Leu Ile Ile Ser Val Cys Tyr
                195                 200                 205
```

```
Ser Leu Met Ile Arg Arg Leu Arg Gly Val Arg Leu Ser Gly Ser
    210                 215                 220

Arg Glu Lys Asp Arg Asn Leu Arg Arg Ile Thr Arg Leu Val Leu Val
225                 230                 235                 240

Val Val Ala Val Phe Val Gly Cys Trp Thr Pro Val Gln Val Phe Val
                245                 250                 255

Leu Val Gln Gly Leu Gly Val Gln Pro Gly Ser Glu Thr Ala Val Ala
            260                 265                 270

Ile Leu Arg Phe Cys Thr Ala Leu Gly Tyr Val Asn Ser Cys Leu Asn
        275                 280                 285

Pro Ile Leu Tyr Ala Phe Leu Asp Glu Asn Phe Lys Ala Cys Phe Arg
    290                 295                 300

Lys Phe Cys Cys Ala Ser Ser Leu His Arg Glu Met Gln Val Ser Asp
305                 310                 315                 320

Arg Val Arg Ser Ile Ala Lys Asp Val Gly Leu Gly Cys Lys Thr Ser
                325                 330                 335

Glu Thr Val Pro Arg Pro Ala
            340

<210> SEQ ID NO 6
<211> LENGTH: 341
<212> TYPE: PRT
<213> ORGANISM: Homo sapiens

<400> SEQUENCE: 6

Met Pro Ala Thr Ala Pro Ser Cys Pro Ser Gly Ser Arg Ser Pro Ser
1               5                   10                  15

Trp Gly Ser Thr Trp Pro Cys Val Ser Glu Gly Ser Trp Gly Thr Ala
            20                  25                  30

Leu Ser Cys Thr Ser Ser Ser Gly Arg Leu Gly Pro Lys Val Pro Val
        35                  40                  45

Trp His Thr Lys Met Lys Thr Ala Thr Asn Ile Tyr Ile Phe Asn Leu
    50                  55                  60

Ala Leu Ala Asp Thr Leu Val Leu Leu Thr Leu Pro Phe Gln Gly Thr
65                  70                  75                  80

Asp Ile Leu Leu Gly Phe Trp Pro Phe Gly Asn Ala Leu Cys Lys Thr
                85                  90                  95

Val Ile Ala Ile Asp Tyr Tyr Asn Met Phe Thr Ser Thr Phe Thr Leu
            100                 105                 110

Thr Ala Met Ser Val Asp Arg Tyr Val Ala Ile Cys His Pro Ile Arg
        115                 120                 125

Ala Leu Asp Val Arg Thr Ser Ser Lys Ala Gln Ala Val Asn Val Ala
    130                 135                 140

Ile Trp Ala Leu Ala Ser Val Val Gly Val Pro Val Ala Ile Met Gly
145                 150                 155                 160

Ser Ala Gln Val Glu Asp Glu Glu Ile Glu Cys Leu Val Glu Ile Pro
                165                 170                 175

Thr Pro Gln Asp Tyr Trp Gly Pro Val Phe Ala Ile Cys Ile Phe Leu
            180                 185                 190

Phe Ser Phe Ile Val Pro Val Leu Val Ile Ser Val Cys Tyr Ser Leu
        195                 200                 205

Met Ile Arg Arg Leu Arg Gly Val Arg Leu Leu Ser Gly Ser Arg Glu
    210                 215                 220

Lys Asp Arg Asn Leu Arg Arg Ile Thr Arg Leu Val Leu Val Val Val
225                 230                 235                 240
```

```
Ala Val Phe Val Gly Cys Trp Thr Pro Val Gln Val Phe Val Leu Ala
                245                 250                 255

Gln Gly Leu Gly Val Gln Pro Ser Ser Glu Thr Ala Val Ala Ile Leu
            260                 265                 270

Arg Phe Cys Thr Ala Leu Gly Tyr Val Asn Ser Cys Leu Asn Pro Ile
        275                 280                 285

Leu Tyr Ala Phe Leu Asp Glu Asn Phe Lys Ala Cys Phe Arg Lys Phe
    290                 295                 300

Cys Cys Ala Ser Ala Leu Arg Arg Asp Val Gln Val Ser Asp Arg Val
305                 310                 315                 320

Arg Ser Ile Ala Lys Asp Val Ala Leu Ala Cys Lys Thr Ser Glu Thr
                325                 330                 335

Val Pro Arg Pro Ala
            340

<210> SEQ ID NO 7
<211> LENGTH: 365
<212> TYPE: PRT
<213> ORGANISM: Homo sapiens

<400> SEQUENCE: 7

Met Glu Pro Leu Phe Pro Ala Pro Phe Trp Glu Val Ile Tyr Gly Ser
1               5                   10                  15

His Leu Gln Gly Asn Leu Ser Leu Ser Pro Asn His Ser Leu Leu
            20                  25                  30

Pro Pro His Leu Leu Leu Asn Ala Ser His Gly Ala Phe Leu Pro Leu
        35                  40                  45

Gly Leu Lys Val Thr Ile Val Gly Leu Tyr Leu Ala Val Cys Val Gly
    50                  55                  60

Gly Leu Leu Gly Asn Cys Leu Val Met His Thr Lys Met Lys Thr Ala
65                  70                  75                  80

Thr Asn Ile Tyr Ile Phe Asn Leu Ala Leu Ala Asp Thr Leu Val Leu
                85                  90                  95

Leu Thr Leu Pro Phe Gln Gly Thr Asp Ile Leu Leu Gly Phe Trp Pro
            100                 105                 110

Phe Gly Asn Ala Leu Cys Lys Thr Val Ile Ala Ile Asp Tyr Tyr Asn
        115                 120                 125

Met Phe Thr Ser Thr Phe Thr Leu Thr Ala Met Ser Val Asp Arg Tyr
    130                 135                 140

Val Ala Ile Cys His Pro Ile Arg Ala Leu Asp Val Arg Thr Ser Ser
145                 150                 155                 160

Lys Ala Gln Ala Val Asn Val Ala Ile Trp Ala Leu Ala Ser Val Val
                165                 170                 175

Gly Val Pro Val Ala Ile Met Gly Ser Ala Gln Val Glu Asp Glu Glu
            180                 185                 190

Ile Glu Cys Leu Val Glu Ile Pro Thr Pro Gln Asp Tyr Trp Gly Pro
        195                 200                 205

Val Phe Ala Ile Cys Ile Phe Leu Phe Ser Phe Ile Val Pro Val Leu
    210                 215                 220

Val Ile Ser Val Cys Tyr Ser Leu Met Ile Arg Arg Leu Arg Gly Val
225                 230                 235                 240

Arg Leu Leu Ser Gly Ser Arg Glu Lys Asp Arg Asn Leu Arg Arg Ile
                245                 250                 255

Thr Arg Leu Val Leu Val Val Val Ala Val Phe Val Gly Cys Trp Thr
```

-continued

```
                    260                 265                 270
       Pro Val Gln Val Phe Val Leu Ala Gln Gly Leu Gly Val Gln Pro Ser
               275                 280                 285

Ser Glu Thr Ala Val Ala Ile Leu Arg Phe Cys Thr Ala Leu Gly Tyr
               290                 295                 300

Val Asn Ser Cys Leu Asn Pro Ile Leu Tyr Ala Phe Leu Asp Glu Asn
       305                 310                 315                 320

Phe Lys Ala Cys Phe Arg Lys Phe Cys Cys Ala Ser Ala Leu Arg Arg
                       325                 330                 335

Asp Val Gln Val Ser Asp Arg Val Arg Ser Ile Ala Lys Asp Val Ala
                   340                 345                 350

Leu Ala Cys Lys Thr Ser Glu Thr Val Pro Arg Pro Ala
               355                 360                 365

<210> SEQ ID NO 8
       <211> LENGTH: 2634
       <212> TYPE: DNA
       <213> ORGANISM: mus musculus

<400> SEQUENCE: 8
tttggcttcc ttctccaacc tgcgcagccc ctccttctct cagccgcagc cttctgcccc      60 tccccttct ggctgccgca ctggctgctg cgtctagtca atatcttatc ttcggagcag      120
gagctaggag ccattcccag ccggagcaga ccccaagcta gagtgagaag cattactcag      180
ttcattgtgc tcctgcctgc ctttctgcta agcattaggg tctgttttgg cccagcttct      240
gaagaggttg tgtgtgctgt tggaggaact gtactgagtg gctttgcagg gtgacagcat      300
ggagtccctc tttcctgccc cattctggga ggtcttgtat ggcagccact ttcaagggaa      360
cctgtctctc ctaaatgaga ccgtaccca tcacctgctc ctcaatgcta gccacagtgc      420
cttcctgccc cttggactca aggtcaccat cgtgggctc tacttggctg tgtgcatcgg      480
ggggctcctg gggaactgcc tcgtcatgta tgtcatcctc agctgggagg gcattgaggg      540
gaactggaga cagcaggcac accaagatga agactgctac caacatttac atatttaatc      600
tggcactggc tgatacccty gtcttgctga cactgcccctt ccagggcaca gacatccttc      660
tgggcttctg gccatttggg aatgcactgt gcaagacggt cattgctatc gactactaca      720
acatgtttac cagcactttc actttgactg ccatgagtgt agaccgttat gtagctatct      780
gccaccctat ccgtgccctt gatgttcgga catccagtaa agcccaggcc gttaatgtgg      840
ccatatgggc cctggcttcg gtggttggtg ttcctgttgc catcatgggc tcagcacaag      900
tggaggatga agagatcgag tgcctggtgg agatccccgc ccctcaggac tattggggcc      960
ctgtatttgc catctgcatc ttcctttttt ccttcatcat cccggttctg atcatctctg     1020
tctgctacag cctcatgatt cgacgacttc gtggtgtccg gctgctttca ggctcccgag     1080
agaaggaccg gaacctgcga cgcatcacac ggctggtact ggtagttgtg ctgtgtttg     1140 tgggctgctg gacacctgtg caggtctttg tcctggttca aggactgggt gttcagccag     1200
gtagtgagac tgcagtagcc attctgcgct ctgcacagc cctgggctat gtcaacagtt     1260
gtctcaatcc cattctctat gctttcttgg atgagaactt caaggcctgc tttagaaagt     1320
tctgctgtgc ttctgccctg caccgggaga tgcaggtttc tgatcgtgtg cgcagcattg     1380
ccaaggatgt aggccttggt tgcaagacct ctgagacagt accacggccg gcatgactag     1440
gcgtggacct gcccatggtg cctgtcagtc ctagaggaag accttttagc accatgggac     1500
aggtcaaagc atcaaggtgg cctccatggc tctgtcagat taagtttcct ccctggtata     1560
```

```
ggaccagaga gaaccaaagg aactgcatgg aaacatccac aactcagtgg acatgcctgg   1620
tgaacccatg taggtattca tggttcactt gactcttctc tggtttctcc ctgctgccct   1680
ggttctaggt gggctcagct gaggtattgt agttgtcatg tagtcactat tgtgactacc   1740
tgttgtgtgc tattgccctc agccttcagt gtttgcacag aactggtgat catacccagt   1800
gttgcctggc ccttaagctt ggagttgcct tggagcatct agttctgact ccactgatgc   1860
attcagatta cctgaggtgg gtgagcatca gtgggttctt ggatgactgt ttcctgacga   1920 ttctttcat gctgtactat ggtgtatatg aaggggactt cacacttcat ctggtactgc   1980
cactgcctgc tctaccaacc tggaccacct tctcagcaag aggctagcag ggggacaaga   2040
cacaaagctt ccctaaggct ctttccctcc aaaaccactg tgaactctta ttctacagac   2100
tgtttggcaa gccctgcttc taactgtgtg ggaagtaatc aggagaaaat tctgtggcct   2160
ctgtaggctg ctcacagcat ggaggcacca catgctggtc ttgggtatgt gtcttggctg   2220
ctcagtatgg gcagggcagg gcacgagact atctctctcc ttattctcca cagcctccct   2280
cagctctcca gcagtcgctc ttttacttga cagtagaggt tagcagcagt tgtactcgta   2340
gaaacacact tgtagcccgg gaagactgga gtcaggatgt gttctattct atacccacag   2400
tgaccacctg cttcatttat agggttagga catatccaag caaggcctgg gcttggcatc   2460
aaatgaagag ctggtatgag agctgaagcc taaaatggct catttgagca atctgcaagg   2520
actattacgg ttttggggac attggaagaa gagtcgatac cttggagata tattgttggt   2580
tcacagaaga agaggctttg taaatgccct ttctatgggt cagataaaaa aaaa          2634
```

<210> SEQ ID NO 9
<211> LENGTH: 1256
<212> TYPE: DNA
<213> ORGANISM: mus musculus

<400> SEQUENCE: 9

```
tggcttttgca gggtgacagc atggagtccc tctttcctgc cccattctgg gaggtcttgt     60
atggcagcca ctttcaaggg aacctgtctc tcctaaatga gaccgtaccc catcacctgc    120
tcctcaatgc tagccacagt gccttcctgc cccttggact caaggtcacc atcgtggggc    180
tctacttggc tgtgtgcatc gggggctcc tggggaactg cctcgtcatg tatgtcatcc    240
tcaggcagtg ccctgaaaac cctctgagag gagtcttaag agagactgag gagagaagac    300
gcatctctct ctcttgattc cttccacaaa ttcacattca ggcacaccaa gatgaagact    360
gctaccaaca tttacatatt taatctggca ctggctgata ccctggtctt gctgacactg    420
cccttccagg gcacagacat ccttctgggc ttctggccat tgggaatgc actgtgcaag    480 acggtcattg ctatcgacta ctacaacatg tttaccagca cttcactttt gactgccatg    540
agtgtagacc gttatgtagc tatctgccac cctatccgtg cccttgatgt tcggacatcc    600
agtaaagccc aggccgttaa tgtggccata tgggccctgg cttcgtggt tggtgttcct    660 gttgccatca tgggctcagc acaagtggag gatgaagaga tcgagtgcct ggtggagatc    720
cccgcccctc aggactattg gggccctgta tttgccatct gcatcttcct tttttccttc    780
atcatcccgg ttctgatcat ctctgtctgc tacagcctca tgattcgacg acttcgtggt    840
gtccggctgc tttcaggctc ccgagagaag gaccggaacc tgcgacgcat cacgcggctg    900
gtactggtag ttgtggctgt gtttgtgggc tgctggacac ctgtgcaggt cttttgtcctg    960 gttcaaggac tgggtgttca gccaggtagt gagactgcag tagccattct gcgcttctgc   1020
```

-continued

| | |
|---|---|
| acagccctgg gctatgtcaa cagttgtctc aatcccattc tctatgcttt cttggatgag | 1080 |
| aacttcaagg cctgctttag aaagttctgc tgtgcttctg ccctgcaccg ggagatgcag | 1140 |
| gtttctgatc gtgtgcgcag cattgccaag gatgtaggcc ttggttgcaa gacctctgag | 1200 |
| acagtaccac ggccggcatg actaggcgtg gacctgccca tggtgcctgt cagtcc | 1256 |

<210> SEQ ID NO 10
<211> LENGTH: 2518
<212> TYPE: DNA
<213> ORGANISM: mus musculus

<400> SEQUENCE: 10

| | |
|---|---|
| tggcttttgca gggtgacagc atggagtccc tctttcctgc cccattctgg gaggtcttgt | 60 |
| atggcagcca ctttcaaggg aacctgtctc tcctaaatga gaccgtaccc catcacctgc | 120 |
| tcctcaatgc tagccacagt gccttcctgc cccttggact caaggtcacc atcgtggggc | 180 |
| tctacttggc tgtgtgcatc gggggctcc tggggaactg cctcgtcatg tatgtcatcc | 240 |
| tcagacaaca ttgtgcactt ggaagatctt tgatgaactt tacaggcagt gccctgaaaa | 300 |
| ccctctgaga ggagtcttaa gagagactga ggagagaaga cagcatctct ctctcttgat | 360 |
| tccttccaca aattcacatt caggcacacc aagatgaaga ctgctaccaa catttacata | 420 |
| tttaatctgg cactggctga taccctggtc ttgctgcaca tgcccttcca gggcacagac | 480 |
| atccttctgg gcttctggcc atttgggaat gcactgtgca agacggtcat tgctatcgac | 540 |
| gctatctgcc accctatccg tgcccttgat gttcggacat ccagtaaagc ccaggccgtt | 600 |
| aatgtggcca tatgggccct ggcttcggtg gttggtgttc ctgttgccat catgggctca | 660 |
| gcacaagtgg aggatgaaga gatcgagtgc ctggtggaga tccccgcccc tcaggactat | 720 |
| tggggccctg tatttgccat ctgcatcttc ctttttttcct tcatcatccc ggttctgatc | 780 |
| atctctgtct gctacagcct catgattcga cgacttcgtg gtgtccggct gctttcaggc | 840 |
| tcccgagaga aggaccggaa cctgcgacgc atcacacggc tggtactggt agttgtggct | 900 |
| gtgtttgtgg gctgctggac acctgtgcag gtctttgtcc tggttcaagg actgggtgtt | 960 |
| cagccaggta gtgagactgc agtagccatt ctgcgcttct gcacagccct gggctatgtc | 1020 |
| aacagttgtc tcaatcccat tctctatgct tccttggatg agaacttcaa ggcctgctttt | 1080 |
| agaaagttct gctgtgcttc tgccctgcac cgggagatgc aggtttctga tcgtgtgcgc | 1140 |
| agcattgcca aggatgtagg ccttggttgc aagacctctg acagtacc acggccggca | 1200 |
| tgactaggcg tggacctgcc catggtgcct gtcagtccac agagcccatc tacacccaac | 1260 |
| acggagctca cacaggtcac tgctctctag gttgaccctg aactgagcgt ctggggcctt | 1320 |
| gaatggcttt tcttttggtt caggatgctc agtcctagag aagacctttt agcaccatg | 1380 |
| ggacaggtca agcatcaag gtggcctcca tggctctgtc agattaagtt tcctccctgg | 1440 |
| tataggacca gagagaacca aggaactgc atggaaacat ccacaactca gtggacatgc | 1500 |
| ctggtgaacc catgtaggta ttcatggttc acttgactct tctctggttt ctccctgctg | 1560 |
| ccctggttct agtgtgggctc agctgaggta ttgtagttgt catgtagtca ctattgtgac | 1620 |
| tacctgttgt gtgctattgc cctcagcctt cagtgtttgc acagaactgg tgatcatacc | 1680 |
| cagtgttgcc tggcccttaa gcttggagtt gccttggagc atctagttct gactccactg | 1740 |
| atgcattcag attacctgag gtgggtgagc atcagtgggt tcttggatga ctgttctcctg | 1800 |
| acgattcttt tcatgctgta ctatggtgta tatgaagggg acttcacact tcatctggta | 1860 |
| ctgccactgc ctgctctacc aacctggacc accttctcag caagaggcta gcaggggggac | 1920 |

-continued

```
aagacacaaa gcttccctaa ggctcttttcc ctccaaaacc actgtgaact cttattctac    1980
agactgtttg gcaagccctg cttctaactg tgtgggaagt aatcaggaga aaattctgtg    2040
gcctctgtag gctgctcaca gcatggaggc accacatgct ggtcttgggt atgtgtcttg    2100
gctgctcagt atgggcaggg cagggcacga gactatctct ctccttattc tccacagcct    2160
ccctcagctc tccagcagtc gctcttttac ttgacagtag aggttagcag cagttgtact    2220
cgtagaaaca cacttgtagc ccgggaagac tggagtcagg atgtgttcta ttctataccc    2280
acagtgacca cctgcttcat ttatagggtt aggacatatc caagcaaggc ctgggcttgg    2340
catcaaatga agagctggta tgagagctga agcctaaaat ggctcatttg agcaatctgc    2400
aaggactatt acggttttgg ggacattgga agaagagtcg ataccttgga gatatattgt    2460
tggttcacag aagaagaggc tttgtaaatg ccctttctat gggtcagata aaaaaaaa    2518
```

<210> SEQ ID NO 11
<211> LENGTH: 1223
<212> TYPE: DNA
<213> ORGANISM: mus musculus

<400> SEQUENCE: 11

```
gtactgagtg gctttgcagg gtgacagcat ggagtccctc tttcctgctc catactggga     60
ggtcttgtat ggcagccact ttcaagggaa cctgtccctc ctaaatgaga ccgtacccca    120
ccacctgctc ctcaatgcta gtcacagcgc cttcctgccc cttggactca aggtcaccat    180
cgtggggctc tacttggctg tgtgcatcgg ggggctcctg gggaactgcc tcgtcatgta    240
tgtcatcctc agctgggagg gcattgaggg ggactggaga cagcaggcac accaagatga    300
agacagctac caacatttac atatttaatc tggcactggc tgatacccctg gtcttgctaa    360 cactgccctt ccagggcaca gacatcctac tgggcttctg gccatttggg aatgcactct    420
gcaagactgt cattgctatc gactactaca acatgtttac cagcactttt actctgaccg    480
ccatgagcgt agaccgctat gtggctatct gccaccctat ccgtgccctt gatgttcgga    540
catccagcaa agcccaggct gttaatgtgg ccatatgggc cctggcttca gtggttggtg    600
ttcctgttgc catcatgggt tcagcacaag tggaagatga agagatcgag tgcctggtgg    660
agatccctgc ccctcaggac tattggggcc ctgtattcgc catctgcatc ttcctttttt    720
ccttcatcat ccctgtgctg atcatctctg tctgctacag cctcatgatt cgacgacttc    780
gtggtgtccg tctgctttca ggctcccggg agaaggaccg aaacctgcgg cgtatcactc    840
gactggtgct ggtagtggtg gctgtgtttg tgggctgctg gacgcctgtg caggtgtttg    900
tcctggttca aggactgggt gttcagccag gtagtgagac tgcagttgcc atcctgcgct    960
tctgcacagc cctgggctat gtcaacagtt gtctcaatcc cattctctat gctttcctgg    1020
atgagaactt caaggcctgc tttagaaagt tctgctgtgt tcatccctg cacgggaga    1080 tgcaggtttc tgatcgtgtg cggagcattg ccaaggatgt tggccttggt tgcaagactt    1140
ctgagacagt accacggcca gcatgactag gcgtggacct gcccatggtg cctgtcagcc    1200
ctgaaccttg agcatctgga gcc                                              1223
```

<210> SEQ ID NO 12
<211> LENGTH: 1283
<212> TYPE: DNA
<213> ORGANISM: Rat

<400> SEQUENCE: 12

-continued

| | |
|---|---|
| gtactgagtg gctttgcagg gtgacagcat ggagtccctc tttcctgctc catactggga | 60 |
| ggtcttgtat ggcagccact ttcaagggaa cctgtccctc ctaaatgaga ccgtacccca | 120 |
| ccacctgctc ctcaatgcta gtcacagcgc cttcctgccc cttggactca aggtcaccat | 180 |
| cgtggggctc tacttggctg tgtgcatcgg ggggctcctg gggaactgcc tcgtcatgta | 240 |
| tgtcatcctc agctgggagg gcattgaggg ggactggaga cagcaggcac accaagatga | 300 |
| agacagctac caacatttac atatttaatc tggcactggc tgatacccct gtcttgctaa | 360 |
| cactgccctt ccagggcaca gacatcctac tgggcttctg gccatttggg aatgcactct | 420 |
| gcaagactgt cattgctatc gactactaca acatgtttac cagcactttt actctgaccg | 480 |
| ccatgagcgt agaccgctat gtggctatct gccaccctat ccgtgccctt gatgttcgga | 540 |
| catccagcaa agcccaggct gttaatgtgg ccatatgggc cctggcttca gtggttggtg | 600 |
| ttcctgttgc catcatgggt tcagcacaag tggaagatga agagatcgag tgcctggtgg | 660 |
| agatccctgc ccctcaggac tattggggcc ctgtattcgc catctgcatc ttccttttt | 720 |
| ccttcatcat ccctgtgctg atcatctctg tctgctacag cctcatgatt cgacgacttc | 780 |
| gtggtgtccg tctgctttca ggctcccggg agaaggaccg aaacctgcgg cgtatcactc | 840 |
| gactggtgct ggtagtggtg gctgtgtttg tgggctgctg gacgcctgtg caggtgtttg | 900 |
| tcctggttca aggactgggt gttcagccag gtagtgagac tgcagttgcc atcctgcgct | 960 |
| tctgcacagc cctgggctat gtcaacagtt gtctcaatcc cattctctat gctttcctgg | 1020 |
| atgagaactt caaggcctgc tttagaaagt ctgctgtgtc ttcatccctg caccgggaga | 1080 |
| tgcaggtttc tgatcgtgtg cggagcattg ccaaggatgt tggccttggt tgcaagactt | 1140 |
| ctgagacagt accacggcca gcatgactag gcgtggacct gcccatggtg cctgtcagcc | 1200 |
| cacagagccc atctacaccc aacacggagc tcacacaggt cactgctctc taggttgacc | 1260 |
| ctgaaccttg agcatctgga gcc | 1283 |

<210> SEQ ID NO 13
<211> LENGTH: 1177
<212> TYPE: DNA
<213> ORGANISM: homo sapiens

<400> SEQUENCE: 13

| | |
|---|---|
| ttgcagggca gtggcatgga gcccctcttc cccgcgccgt tctgggaggt tatctacggc | 60 |
| agccaccttc agggcaacct gtccctcctg agccccaacc acagtctgct gccccgcat | 120 |
| ctgctgctca atgccagcca cggcgccttc ctgcccctcg ggctcaaggt caccatcgtg | 180 |
| gggctctacc tggccgtgtg tgtcggaggg ctcctgggga actgccttgt catgtacgtc | 240 |
| atcctcaggt aggctgggcc ccaaggttcc tgtctggcac accaaaatga agacagccac | 300 |
| caatatttac atctttaacc tggccctggc cgacactctg gtcctgctga cgctgccctt | 360 |
| ccagggcacg gacatcctcc tgggcttctg gccgtttggg aatgcgctgt gcaagacagt | 420 |
| cattgccatt gactactaca acatgttcac cagcaccttc accctaactg ccatgagtgt | 480 |
| ggatcgctat gtagccatct gccacccat ccgtgccctc gacgtccgca cgtccagcaa | 540 |
| agcccaggct gtcaatgtgg ccatctgggc cctggcctct gttgtcggtg ttcccgttgc | 600 |
| catcatgggc tcggcacagg tcgaggatga agagatcgag tgcctggtgg agatccctac | 660 |
| ccctcaggat tactgggggcc cggtgtttgc catctgcatc ttcctcttct ccttcatcgt | 720 |
| ccccgtgctc gtcatctctg tctgctacag cctcatgatc cggcggctcc gtggagtccg | 780 |
| cctgctctcg ggctcccgag agaaggaccg gaacctgcgg cgcatcactc ggctggtgct | 840 |

-continued

```
ggtggtagtg gctgtgttcg tgggctgctg gacgcctgtc caggtcttcg tgctggccca      900
agggctgggg gttcagccga gcagcgagac tgccgtggcc attctgcgct tctgcacggc      960
cctgggctac gtcaacagct gcctcaaccc catcctctac gccttcctgg atgagaactt     1020
caaggcctgc ttccgcaagt tctgctgtgc atctgccctg cgccgggacg tgcaggtgtc     1080
tgaccgcgtg cgcagcattg ccaaggacgt ggccctggcc tgcaagacct ctgagacggt     1140
accgcggccc gcatgactag gcgtggacct gcccatg                              1177
```

<210> SEQ ID NO 14
<211> LENGTH: 1134
<212> TYPE: DNA
<213> ORGANISM: homo sapiens

<400> SEQUENCE: 14

```
ttgcagggca gtggcatgga gcccctcttc cccgcgccgt tctgggaggt tatctacggc       60
agccaccttc agggcaacct gtccctcctg agccccaacc acagtctgct gccccgcat      120 ctgctgctca atgccagcca cggcgccttc ctgcccctcg ggctcaaggt caccatcgtg      180
gggctctacc tggccgtgtg tgtcggaggg ctcctgggga actgccttgt catgcacacc      240
aaaatgaaga cagccaccaa tatttacatc tttaacctgg ccctggccga cactctggtc      300
ctgctgacgc tgcccttcca gggcacggac atcctcctgg gcttctggcc gtttgggaat      360
gcgctgtgca agacagtcat tgccattgac tactacaaca tgttcaccag caccttcacc      420
ctaactgcca tgagtgtgga tcgctatgta gccatctgcc accccatccg tgccctcgac      480
gtccgcacgt ccagcaaagc ccaggctgtc aatgtggcca tctgggccct ggcctctgtt      540
gtcggtgttc ccgttgccat catgggctcg gcacaggtcg aggatgaaga gatcgagtgc      600
ctggtggaga tccctacccc tcaggattac tggggcccgg tgtttgccat ctgcatcttc      660
ctcttctcct tcatcgtccc cgtgctcgtc atctctgtct gctacagcct catgatccgg      720
cggctccgtg gagtccgcct gctctcgggc tcccgagaga aggaccggaa cctgcggcgc      780
atcactcggc tggtgctggt ggtagtggct gtgttcgtgg gctgctggac gcctgtccag      840
gtcttcgtgc tggcccaagg gctgggggtt cagccgagca gcgagactgc cgtggccatt      900
ctgcgcttct gcacggccct gggctacgtc aacagctgcc tcaaccccat cctctacgcc      960
ttcctggatg agaacttcaa ggcctgcttc cgcaagttct gctgtgcatc tgccctgcgc     1020
cgggacgtgc aggtgtctga ccgcgtgcgc agcattgcca aggacgtggc cctggcctgc     1080
aagacctctg agacggtacc gcggcccgca tgactaggcg tggacctgcc catg           1134
```

<210> SEQ ID NO 15
<211> LENGTH: 367
<212> TYPE: PRT
<213> ORGANISM: Mus musculus

<400> SEQUENCE: 15

```
Met Glu Ser Leu Phe Pro Ala Pro Phe Trp Glu Val Leu Tyr Gly Ser
1               5                   10                  15

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45

Val Thr Ile Val Gly Leu Tyr Leu Ala Val Cys Ile Gly Gly Leu Leu
    50                  55                  60
```

Gly Asn Cys Leu Val Met Tyr Val Ile Leu Arg His Thr Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Phe
            100                 105                 110

Trp Pro Phe Gly Asn Ala Leu Cys Lys Thr Val Ile Ala Ile Asp Tyr
            115                 120                 125

Tyr Asn Met Phe Thr Ser Thr Phe Thr Leu Thr Ala Met Ser Val Asp
        130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
            180                 185                 190

Glu Glu Ile Glu Cys Leu Val Glu Ile Pro Ala Pro Gln Asp Tyr Trp
            195                 200                 205

Gly Pro Val Phe Ala Ile Cys Ile Phe Leu Phe Ser Phe Ile Ile Pro
        210                 215                 220

Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
            260                 265                 270

Trp Thr Pro Val Gln Val Phe Val Leu Val Gln Gly Leu Gly Val Gln
            275                 280                 285

Pro Gly Ser Glu Thr Ala Val Ala Ile Leu Arg Phe Cys Thr Ala Leu
        290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ala Leu
                325                 330                 335

His Arg Glu Met Gln Val Ser Asp Arg Val Arg Ser Ile Ala Lys Asp
            340                 345                 350

Val Gly Leu Gly Cys Lys Thr Ser Glu Thr Val Pro Arg Pro Ala
        355                 360                 365

<210> SEQ ID NO 16
<211> LENGTH: 46
<212> TYPE: DNA
<213> ORGANISM: Mus musculus

<400> SEQUENCE: 16
tccagctggg agggcattga ggggaactgg agacagcagg tgagga            46

<210> SEQ ID NO 17
<211> LENGTH: 75
<212> TYPE: DNA
<213> ORGANISM: Mus musculus

<400> SEQUENCE: 17
tgctagacaa cattgtgcac ttggaagatc tttgatgaac tttacaggca gtgccctgaa    60
aaccctctga gagga                                                    75

```
<210> SEQ ID NO 18
<211> LENGTH: 81
<212> TYPE: DNA
<213> ORGANISM: Mus musculus

<400> SEQUENCE: 18
gtcagtgggc agtcctcctc cctgaccaat cagttcccca tggttcttgc cggcccctct      60
gacctcattt ctctcctgca g                                                81

<210> SEQ ID NO 19
<211> LENGTH: 5
<212> TYPE: PRT
<213> ORGANISM: Unknown
<220> FEATURE:
<223> OTHER INFORMATION: linking peptide bridging  carboxy terminus of
      one V region and the amino terminus of another V region

<400> SEQUENCE: 19

Gly Gly Gly Gly Ser
1               5

<210> SEQ ID NO 20
<211> LENGTH: 20
<212> TYPE: DNA
<213> ORGANISM: Mouse

<400> SEQUENCE: 20
tgccttcctg cccttggac                                                   20

<210> SEQ ID NO 21
<211> LENGTH: 21
<212> TYPE: DNA
<213> ORGANISM: Mouse

<400> SEQUENCE: 21
cccagaagga tgtctgtgcc c                                                21

<210> SEQ ID NO 22
<211> LENGTH: 48
<212> TYPE: DNA
<213> ORGANISM: Artificial
<220> FEATURE:
<223> OTHER INFORMATION: probe for KOR-3a used to prepare labelled
      fragment of KOR-3

<400> SEQUENCE: 22
ggtgtgcctg ctgtctccag ttcccctcaa tgccctccca gctgagga                   48

<210> SEQ ID NO 23
<211> LENGTH: 45
<212> TYPE: DNA
<213> ORGANISM: Artificial
<220> FEATURE:
<223> OTHER INFORMATION: probe for KOR-3a used to prepare labelled
      fragment of KOR-3

<400> SEQUENCE: 23
cctcagtctc tcttaagact ctcagagggt tttcagggca ctgcc                      45

<210> SEQ ID NO 24
<211> LENGTH: 20
<212> TYPE: DNA
<213> ORGANISM: Mouse

<400> SEQUENCE: 24
```

```
tcctggggaa ctgcctcgtc                                              20

<210> SEQ ID NO 25
<211> LENGTH: 21
<212> TYPE: DNA
<213> ORGANISM: Mouse

<400> SEQUENCE: 25
cccagaagga tgtctgtgcc c                                            21

<210> SEQ ID NO 26
<211> LENGTH: 76
<212> TYPE: DNA
<213> ORGANISM: Mus musculus

<400> SEQUENCE: 26
gtcttaagag agactgagga gagaagacag catctctctc tcttgattcc ttccacaaat  60
tcacattcag gttaga                                                  76
```